(12) United States Patent
Shachar et al.

(10) Patent No.: US 11,883,203 B2
(45) Date of Patent: Jan. 30, 2024

(54) SKULL-MOUNTED DRUG AND PRESSURE SENSOR

(71) Applicant: Cognos Therapeutics Inc., Los Angeles, CA (US)

(72) Inventors: Yehoshua Shachar, Santa Monica, CA (US); Thomas Chen, La Canada, CA (US); Thomas J. Lobl, Valencia, CA (US); Jeffrey A. Brydle, Pasadena, CA (US); Juan R. Gonzalez, Arleta, CA (US); Virote Indravudh, Santa Clarita, CA (US); Christian Merot, Ventura, CA (US); Allan R. Schwartz, Thousand Oaks, CA (US); Chad Srisathapat, Sun Valley, CA (US)

(73) Assignee: Cognos Therapeutics Inc., Inglewood, CA (US)

( * ) Notice: Subject to any disclaimer, the term of this patent is extended or adjusted under 35 U.S.C. 154(b) by 423 days.

(21) Appl. No.: 16/805,308

(22) Filed: Feb. 28, 2020

(65) Prior Publication Data

US 2020/0196868 A1 Jun. 25, 2020

Related U.S. Application Data

(62) Division of application No. 15/594,251, filed on May 12, 2017, now Pat. No. 10,786,155.

(Continued)

(51) Int. Cl.
*A61B 5/00* (2006.01)
*A61B 5/1459* (2006.01)
(Continued)

(52) U.S. Cl.
CPC .......... *A61B 5/6868* (2013.01); *A61B 5/0031* (2013.01); *A61B 5/03* (2013.01);
(Continued)

(58) Field of Classification Search
CPC ......... A61B 5/0031; A61B 5/03; A61B 5/031; A61B 5/1459; A61B 5/4839;
(Continued)

(56) References Cited

U.S. PATENT DOCUMENTS

2008/0058773 A1* 3/2008 John .................. A61N 1/37235
604/891.1
2009/0306594 A1* 12/2009 Pang ................. A61M 5/14276
307/66

(Continued)

*Primary Examiner* — Lauren P Farrar
(74) *Attorney, Agent, or Firm* — Marcus Dawes

(57) ABSTRACT

A skull-mounted drug and pressure sensor (SOS), a smart pump (ISP) electrically coupled to the SOS and a drug delivery and communications catheter communicating the SOS with the ISP are combined for a first embodiment. A skull-mounted (SOS), a metronomic biofeedback pump (MBP) electrically coupled to the SOS and a drug delivery and communications catheter having a sending and receiving optical fiber communicating the SOS with the MBP are combined for a second embodiment. A third embodiment combines a (SOS), an implantable power and communication unit (PCU) electrically coupled to the SOS, and a drug delivery and communications catheter for communicating the SOS with the PCU and for communicating the exterior source of the drug to the SOS. A fourth embodiment combines a ventricular catheter with a CSF accessible chamber and drug delivery port; and an implantable stand-alone skull-mounted drug and pressure sensor (SPS).

3 Claims, 18 Drawing Sheets

Related U.S. Application Data

(60) Provisional application No. 62/336,446, filed on May 13, 2016.

(51) Int. Cl.
*A61B 5/03* (2006.01)
*A61M 5/142* (2006.01)
*A61M 27/00* (2006.01)
*A61M 5/14* (2006.01)
*A61B 5/01* (2006.01)
*A61M 1/00* (2006.01)
*A61B 90/00* (2016.01)

(52) U.S. Cl.
CPC ............ *A61B 5/031* (2013.01); *A61B 5/1459* (2013.01); *A61B 5/4839* (2013.01); *A61M 5/142* (2013.01); *A61B 5/01* (2013.01); *A61B 2090/064* (2016.02); *A61B 2562/0233* (2013.01); *A61M 1/60* (2021.05); *A61M 5/14* (2013.01); *A61M 27/006* (2013.01)

(58) Field of Classification Search
CPC ... A61B 5/6868; A61B 2090/064; A61B 5/01; A61B 2562/0233; A61M 5/142; A61M 1/0001; A61M 5/14; A61M 27/006
See application file for complete search history.

(56) References Cited

U.S. PATENT DOCUMENTS

| | | | |
|---|---|---|---|
| 2010/0179518 A1* | 7/2010 | Ludvig | A61B 5/24 604/891.1 |
| 2011/0054390 A1 | 3/2011 | Searle | |
| 2015/0011855 A1* | 1/2015 | Burnett | A61M 5/14276 600/365 |

* cited by examiner

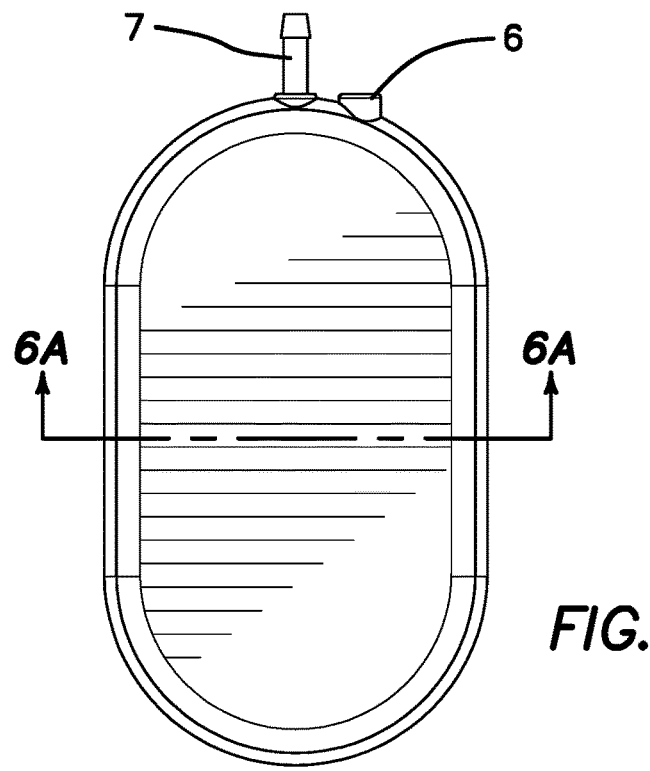
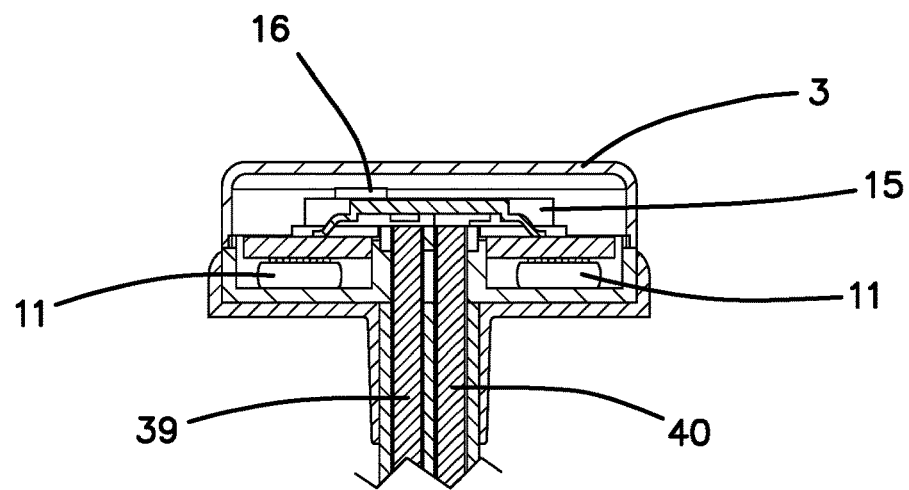
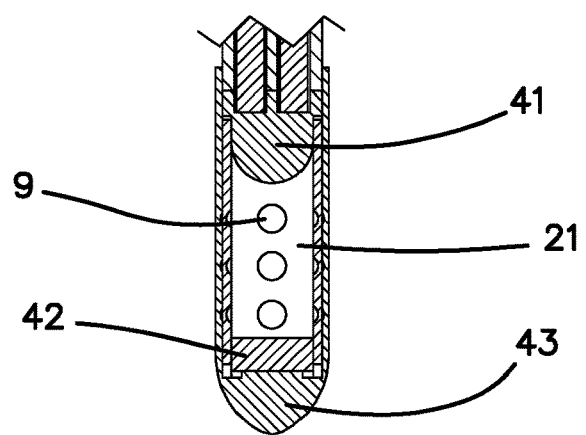
FIG. 6A
FIG. 6B

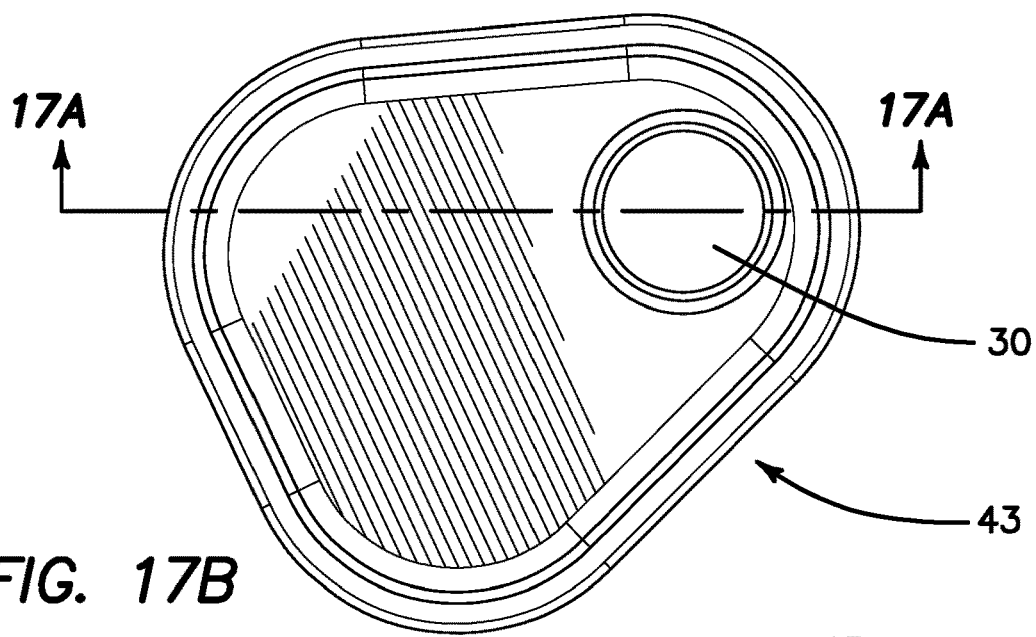
FIG. 17B
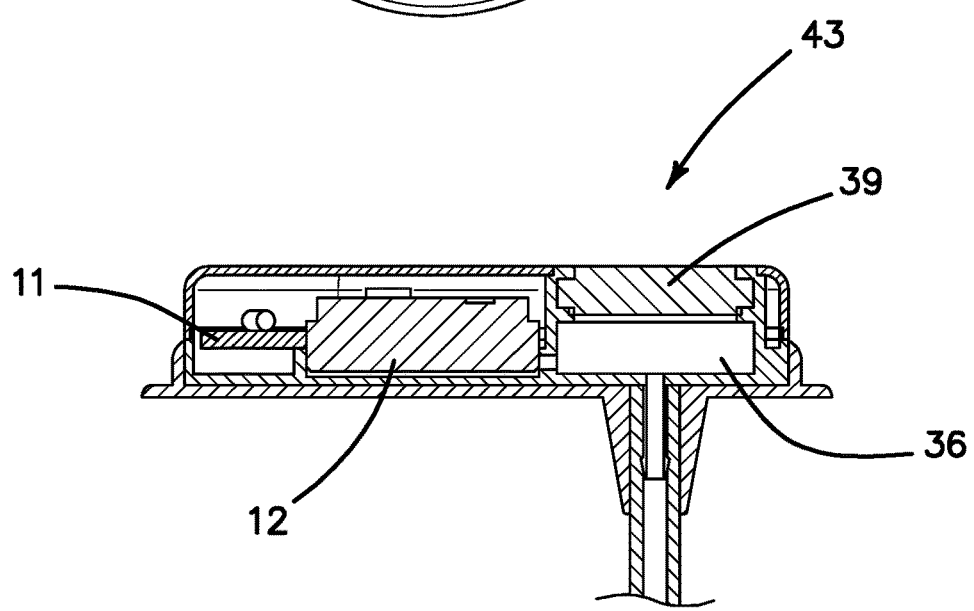
FIG. 17A
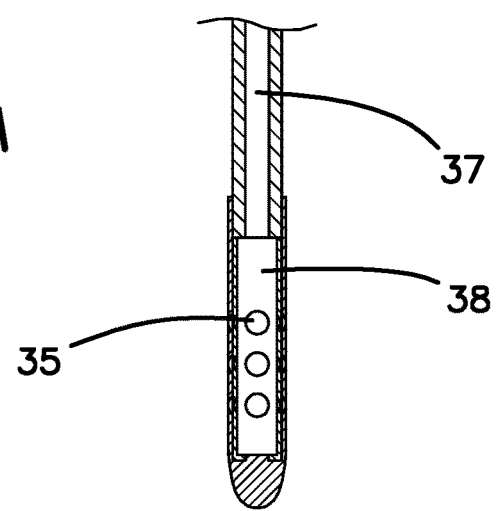

SKULL-MOUNTED DRUG AND PRESSURE SENSOR

RELATED APPLICATIONS

The present application is a divisional of U.S. patent application Ser. No. 15/594,251, filed on May 12, 2017, which in turn is related to U.S. Provisional Patent Application, Ser. No. 62/336,446, filed on May 13, 2016, which are each incorporated herein by reference and to which priority is claimed pursuant to 35 USC 119.

BACKGROUND

Field of the Technology

The invention relates to the field of implantable pumps used in the treatment of brain cancers and neurological disease. It also relates to a skull-mounted drug and pressure sensor (SOS) that has a built-in optical sensor to detect drugs in a chamber built into a catheter that extends from a skull-mounted body of the SOS into the brain.

Description of the Prior Art

An Ommaya reservoir is an intraventricular catheter system that was originally invented in 1963 by Ayub K. Ommaya, a Pakistani neurosurgeon and that can be used for the aspiration of cerebrospinal fluid or for the delivery of drugs (e.g. chemotherapy) into the cerebrospinal fluid. It consists of a catheter disposed in one lateral brain ventricle attached to a reservoir implanted under the scalp. It is used to treat brain tumors, leukemia/lymphoma or leptomeningeal disease by intrathecal drug administration. In the palliative care of terminal cancer, an Ommaya reservoir can be inserted for intraventricular injection of morphine.

Development of the Ommaya reservoir was a significant breakthrough in treatment of brain cancer and neurological disease when it was introduced, as it provided a minimally invasive method for neurosurgeons to bypass the blood brain barrier and deliver drug directly to the brain. However, the major risks associated with the use of the Ommaya reservoir involves infections and complications due to malposition or malfunction of the device. In addition, there can be blockage or leakage of the catheter, which can lead to improper drug delivery and development of lesions along the catheter. The use of Ommaya to deliver chemotherapy drugs by a bolus injection into the brain usually leads to toxic levels of the chemotherapy drug immediately following delivery, a short interval of drug concentration within the therapeutic range followed by long periods of sub-therapeutic drug concentration which could accelerate the development of drug resistance. It is well known that chemotherapy into the brain also can lead to elevated brain CSF pressure and hydrocephalus if not addressed. These problems with use of the Ommaya reservoir for drug delivery are addressed by the inventions described herein.

BRIEF SUMMARY

A first embodiment of the illustrated embodiments is directed to a skull-mounted drug and pressure sensor (SOS) electrically connected to a pump. The SOS has a wired connection to a pump (called implanted smart pump (ISP) in this application) and a drug delivery tube contained in multi-lumen tubing or catheter communicating the SOS with the ISP. The catheter includes a dual lumen tube. The wired connection enables the SOS to be smaller as the ISP has the battery and most, but not all, of the electronics for the SOS is located inside the ISP.

A second embodiment includes an SOS optical sensor (no pressure sensor) connected by optical fibers to the pump. The optical sensor is located inside the metronomic biofeedback pump (MBP) pump casing and the SOS only has the optics to receive the light signal from the pump, send it through the sensing chamber containing the cerebro-spinal fluid (CSF) and return the signal to the pump (called a metronomic biofeedback pump (MBP) in this application) where it will be analyzed. For additional clarity, the MBP has the LEDs, photodiode, the electronic analysis hardware and software within the pump case whereas the ISP does not. In the first embodiment the LEDs, the photodiodes and electronic analysis hardware are in the SOS and not contained within the ISP. The SOS contains the necessary optics to bend the light and connect it to the pump. The MBP contains the LED's light source connected to the fiber optic cables and the receiving photo diode to convert the returning light that has passed through the CSF into an electrical signal that will be analyzed by the electronics included in the MBP. The MBP and the SOS are connected by a tri-lumen tube—one is a drug delivery tube and two fiber optic tubes for sending and receiving light. In this embodiment, the pressure sensor is in the pump. The connector between the MBP and the SOS is tri-laminar tubing. One lumen is for drug delivery to the SOS drug delivery port, and two lumens are for the fiber optic cables; one for sending light from the MBP to the CSF optical chamber and one is for the return light from the chamber back to the MBP to a photodiode and the electronics for calculating the drug concentrations and other necessary data management actions.

A third embodiment is a stand-alone system that includes the optical and pressure sensor (SOS) as described in the first embodiment connected to a power and communication unit (PCU). The PCU is not connected to a pump but communicates wirelessly to an external receiver or mobile system monitor, optionally to a pump and to a clinician programmer. In this embodiment, the SOS is totally "independent" of the pump. The SOS is connected to the power communications unit (PCU) which has a ventricular access port for optional drug delivery to the brain or sampling CSF. The PCU has the battery, and wireless low power Bluetooth electronics for communicating with the outside world. It also has, optionally, additional computational electronics for managing data and data storage. The SOS has the optical sending and receiving and electronics necessary to measure the drug in CSF and communicate that information to the PCU. The information is sent optionally directly to the pump and non-optionally to a mobile system monitor and the clinician programmer. These external devices can optionally communicate with any internal pumps or other implanted devices, but there is no drug delivery catheter or other connection with another device or ability to "close the loop".

A fourth embodiment is directed to a stand-alone skull-mounted pressure sensor (SPS) with a ventricular access port for measuring CSF pressure and drug delivery and providing for electronic communication with the clinical programmer and mobile system monitor. This skull-mounted pressure sensor (SPS) with ventricular access is a less complex SOS. This SPS differs from the SOS in that the separate optical sensor components are removed and it contains a battery, appropriate electronics and a low power Bluetooth communication system to communicate measured brain CSF pressure to an external device. The ventricular access port (VAP) then can be used to relieve the CSF over-pressure by withdrawing CSF fluid. It can also deliver drugs through the VAP to the brain via the fluid pathway on the ventricular catheter. The SPS has a catheter stem (ventricular catheter) that is placed into the ventricle to measure CSF pressure and has fluidic communication with the VAP chamber and from the VAP chamber to the pressure sensor. It is also optionally fitted in subembodiments with a catheter fitted with a valve assembly to deliver CSF fluid to the peritoneal cavity in cases of significant brain over pressure such as in hydrocephalus.

The SOS provides the ability to measure the concentration of a drug in the cerebro-spinal fluid (CSF) at the site of delivery and communicate the data to an external device or to the pump. This significant enhancement over existing Ommaya reservoir technology allows the physician to monitor drug diffusion away from the delivery site, thereby verifying CSF patency and proper placement of the ventricularly placed sensor and drug delivery catheter. The SOS also does not have a reservoir for holding CSF fluid or provide access to CSF fluid via a port as an Ommaya port does unless it is the third embodiment above that is connected to the PCU or the SPS in the fourth embodiment above.

The systems are implanted in between the scalp and the skull with the catheter inserted into the ventricles of the brain. The skull mounted embodiments have a low enough profile not to erupt through the skin when placed on the skull and below the skin or to be uncomfortable (for example: to lay one's head on a pillow) or cause significant skin erosion. In some embodiments where the vertical height is too large (>3 mm) a bone "bed" is carved into the skull of sufficient depth to counter sink the device not to exceed the 3 mm vertical height limit beyond the surface of the skull bone. In some cases, the vertical height limits can be exceeded where the skin is loose and there in less likelihood of eruption through the skin. In addition, and optionally, as part of the deployment of the device, when the height of the device is too high in some embodiments to be acceptable by carving a depression in the skull bone, a hole can be drilled through the skull to enable the profile be lowered sufficiently so the device will not erupt through the skin.

In third embodiment above a septum on the PCU provides the doctor a point for direct delivery of drug and collection of CSF samples. The first and second embodiments above do not have a septum for collecting CSF fluid because the pump is used to provide the drug and there is a catheter access port in the pumping system which allows for the collection of CSF as desired. The SOS implantation protocols are based on existing surgical procedures for Ommaya implantation and for electrical stimulation devices such as Parkinson's disease stimulators that suppress tremor. Once implanted, the SOS can be used as a standalone device to deliver drug via pumps in the first and second embodiments above only or via the injection port in the third and fourth embodiments above only and measure drug concentration at the site of delivery, or paired with an implantable drug delivery pump connected to the proximal end of the delivery catheter. The distal end of the SOS catheter is implanted into the ventricle.

During operation, the device can be run in several modes for data management: 1) concentration data can be delivered immediately after measurement and drug delivery protocols may optionally be altered depending on the information, or 2) it can be set to record a series of measurements over several time points and then after a delay to wirelessly or by wired connection to the ISP transfer the data where it can be further processed. In all cases the information will be communicated to the clinician programmer, the patient management device and to a cloud electronic medical record (EMR) storage site.

All these SOS embodiments optionally have two or more suture anchors (eyelets or "ears" not illustrated) in the device casing or on the biocompatible coating, if present, to act as locations where the surgeons can suture the device to the skull or suitable tissue and ligaments to prevent movement.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIG. 6*a* is a side cross sectional view of the assembled SOS of FIGS. 1-5 as seen through section lines 6B-6B of FIG. 6*b*.

FIG. 6*b* is a top plan view of the SOS of FIG. 1 with the top of the casing in place illustrating section lines 6B-6B.

FIG. 17a is a side cross sectional view of the stand-alone skull-mounted pressure sensor (SPS) of FIG. 15 as seen through section lines 17C-17C of FIG. 17b.

FIG. 17b is a top plan view of stand-alone skull-mounted pressure sensor (SPS) of FIG. 15 with the top of the casing in place illustrated section lines 17C-17C.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED FOUR EMBODIMENTS

Figure 1:
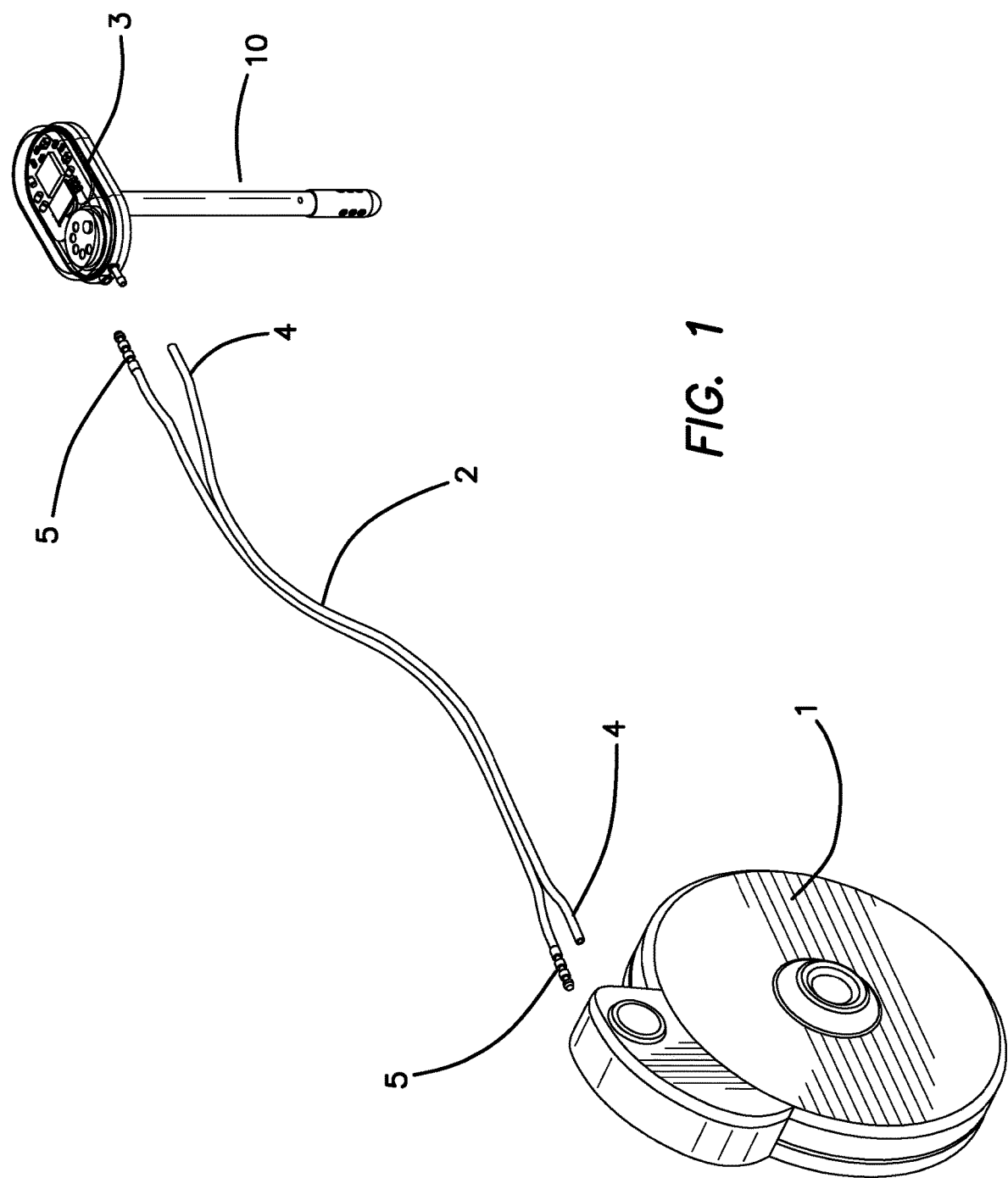
FIG. 1 is an exploded perspective view of the SOS and ISP of the first embodiment.
Figure 2:
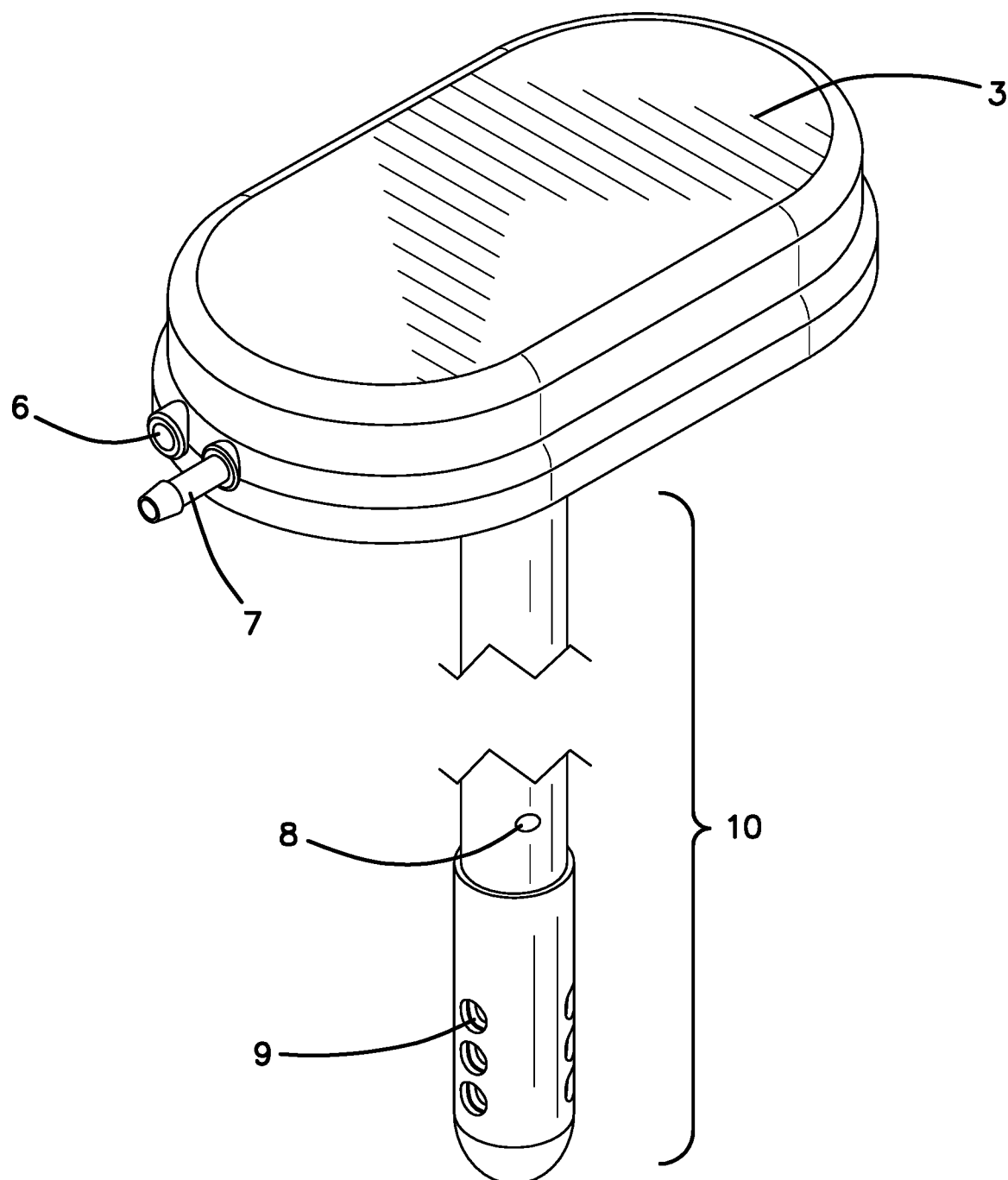
FIG. 2 is an enlarged upper perspective view of the SOS of FIG. 1.

FIG. 1 illustrates perspective view of the ISP 1, the SOS 3, a ventricular catheter 10 for insertion into the brain and a dual lumen drug supply catheter 2 which connects the pump 1 to the SOS 3. The dual lumen catheter includes one lumen 4 for drug delivery and a second lumen 5 for the wires necessary for bidirectional communication between the SOS 3 and the pump 1. The drug delivery catheter lumen 4 connects to the SOS through port 7 and the electronics wires 5 connect via pass through port 6 as illustrated in FIG. 2. A drug or multiple drugs will be provided through catheter lumen 4 coming from an implantable pump 1 or an external pump (not shown) through a pump reservoir (not shown), or through the ventricular access port 30 in the fourth embodiment in FIGS. 15-16, and thence via ventricular catheter 10 into the ventricle emanating from the drug delivery port 8. The CSF/drug sensing chamber 21 shown in FIG. 6 is in fluid communication with the CSF via holes 9 in FIG. 2. These holes 9 allow drug containing CSF to enter the chamber 21 and be analyzed by the optical sensor as described below.

Figure 3:
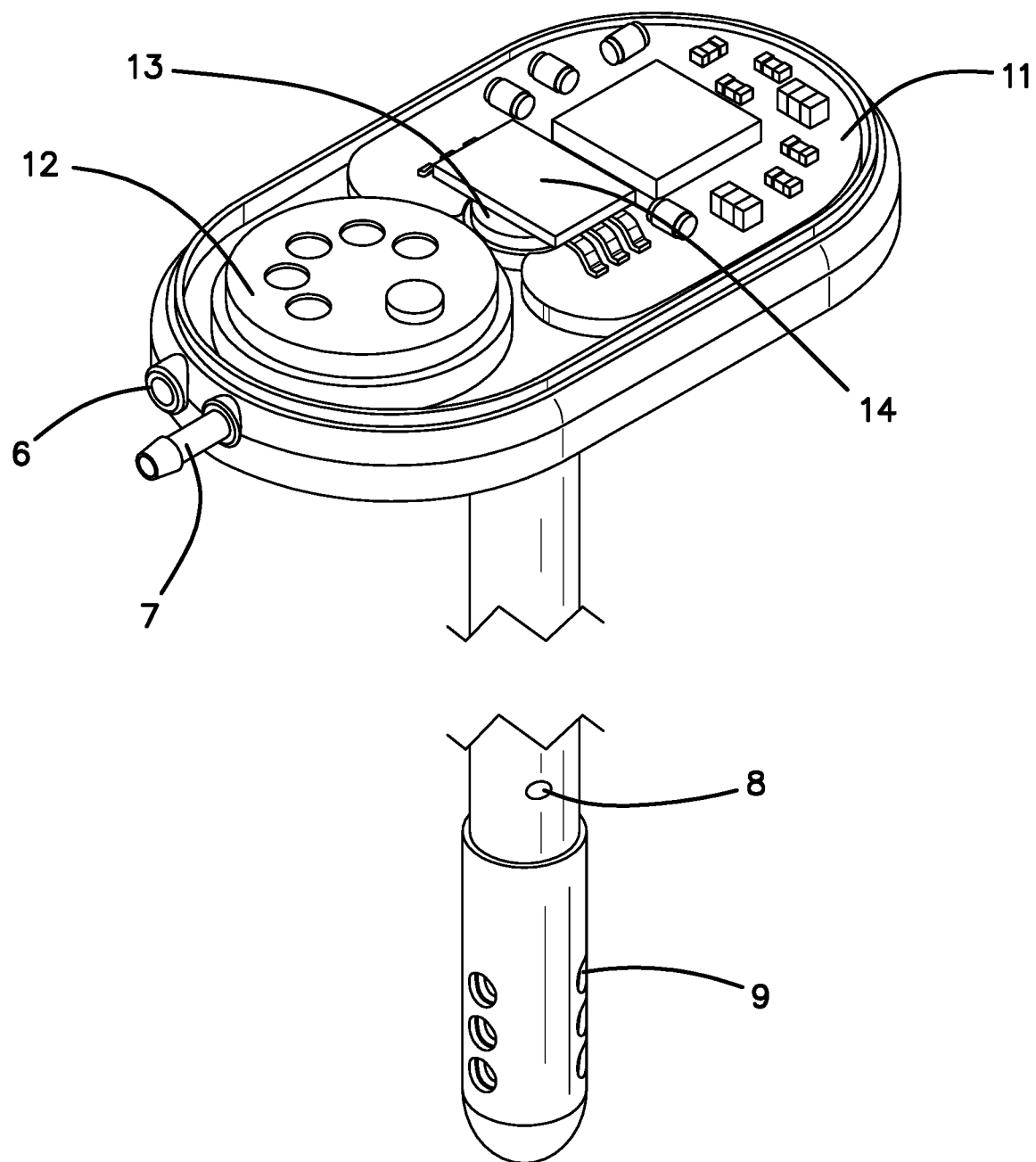
FIG. 3 is an upper perspective view of the SOS of FIG. 2 with the top of the casing removed to expose the pressure sensor and electronics disposed therein.
Figure 4:
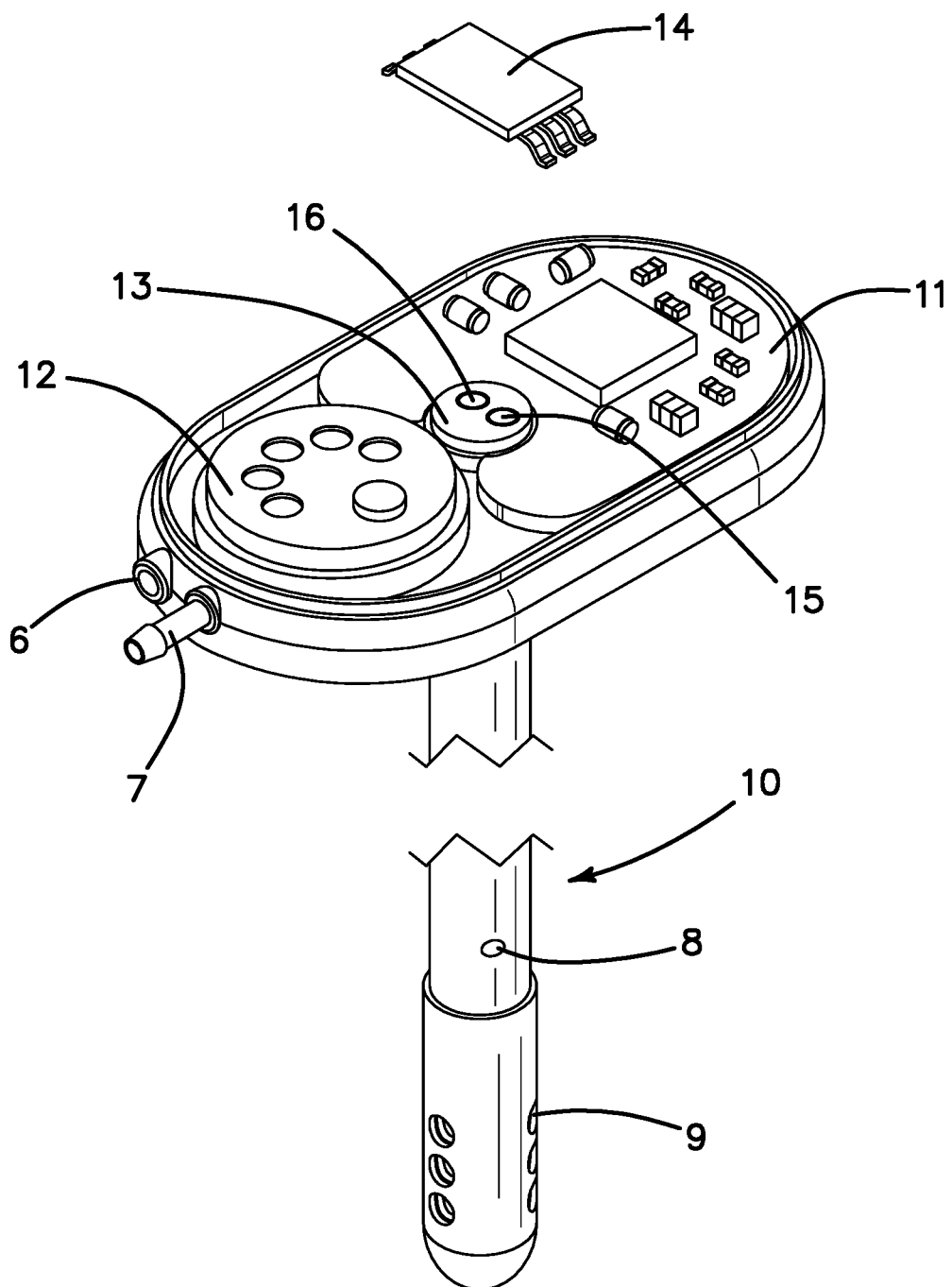
FIG. 4 is an upper perspective view of the SOS of FIG. 3 with the LED chip shown in exploded view to illustrate the fiber optic ports located below the LED chip.
Figure 5:
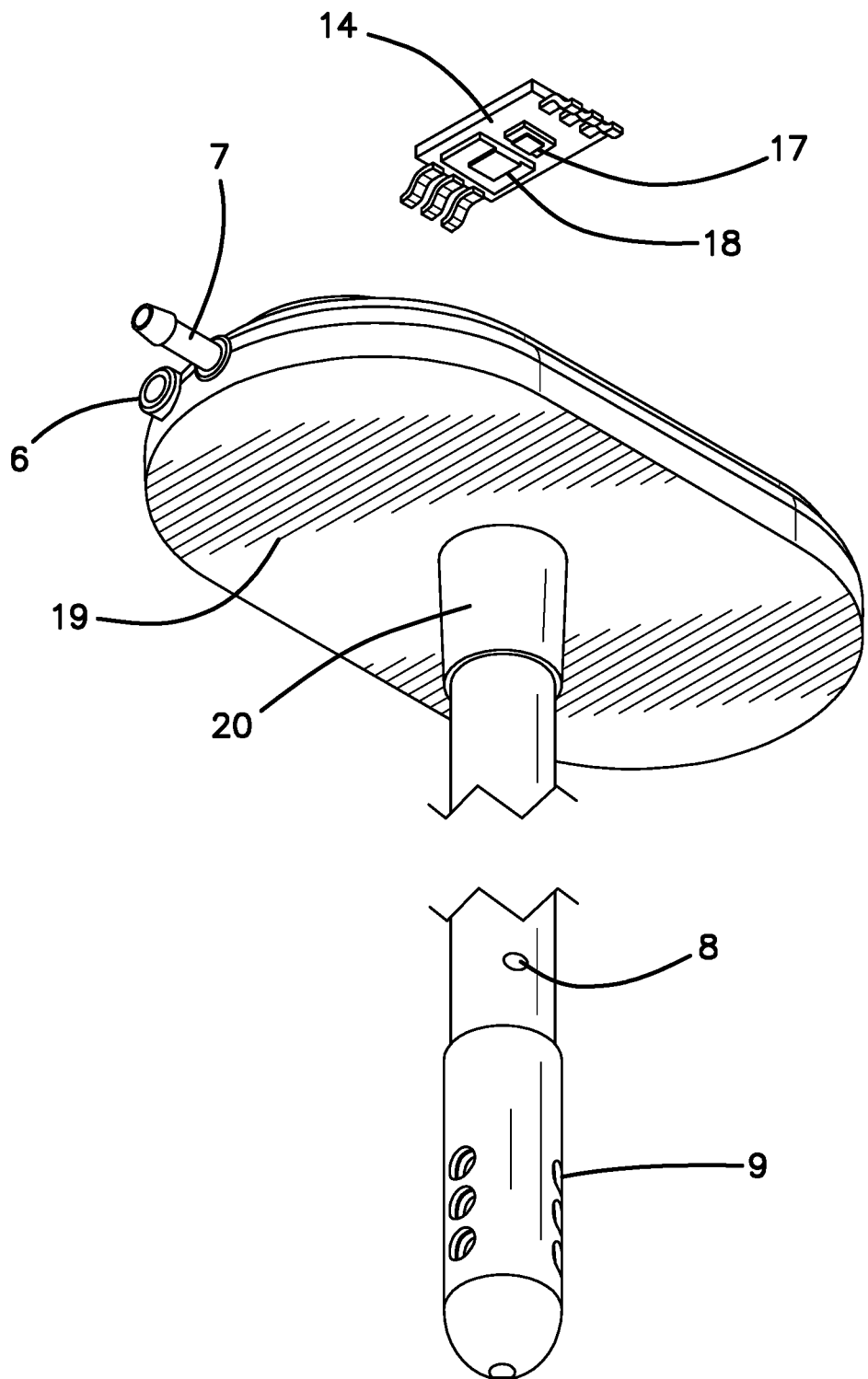
FIG. 5 is a lower perspective view of the SOS of FIG. 4 with the LED chip shown in exploded view.

FIG. 3 is a cut away perspective drawing of the SOS 3 with the top cover removed showing the pressure sensor 12 which measures CSF pressure and also confirms that there is no leak's or obstruction in the catheter or leakage in key connections. The electronics board 11's and the optical sensor 13's location and LED breadboard 14 for the SOS are also illustrated in FIGS. 3 and 4. FIG. 4 provides a less obstructed view of the optical sensor where the LED breadboard 14 has been removed to show the LED origination fiber 16 and the reflected light returning optical fiber 15. A perspective bottom view of the LED breadboard 14 is shown in FIG. 5 illustrating the source for the LED sending unit 17 and photodiode receiving unit 18. FIG. 5 also illustrates the silicone skull seat 19 which provides a biocompatible coating to the bottom of the SOS and a strain relief seat 20 which provides extra support for the ventricular catheter 10 extending from the SOS.

FIG. 6a is a perpendicular side cross sectional view taken through section lines 6B-6B of FIG. 6b showing a more detailed view of the device and especially illustrating the fiber optic pathway. The source LED 16 is attached to the proximal end of the sending fiber optic fiber 39 which goes through to the lens 41 which then transmits the light through the sensing chamber 21 to the distal reflective mirror 42. The light beam then transverses the sensing chamber 21 again essentially doubling the path length of the sensing distance to the lens 41 and then back up through the receiving fiber optic 40 to the receiving photodiode 15. The bullet tip 43 covers the end of the sensing chamber 21 and the reflective mirror 42 and allows for a minimally destructive penetration of brain tissue on insertion of the ventricular catheter 10. The sensing chamber 21 has holes 9 cut through its walls to allow for free diffusion of CSF fluid containing drug into and out of the sensing chamber 21. The electronics board and components 11 are placed at the bottom of the hermetically sealed SOS device and leave room for the pressure sensor 12 which is in fluid communication with the ventricular catheter 10 and the sensing chamber 21.

Figure 7B:
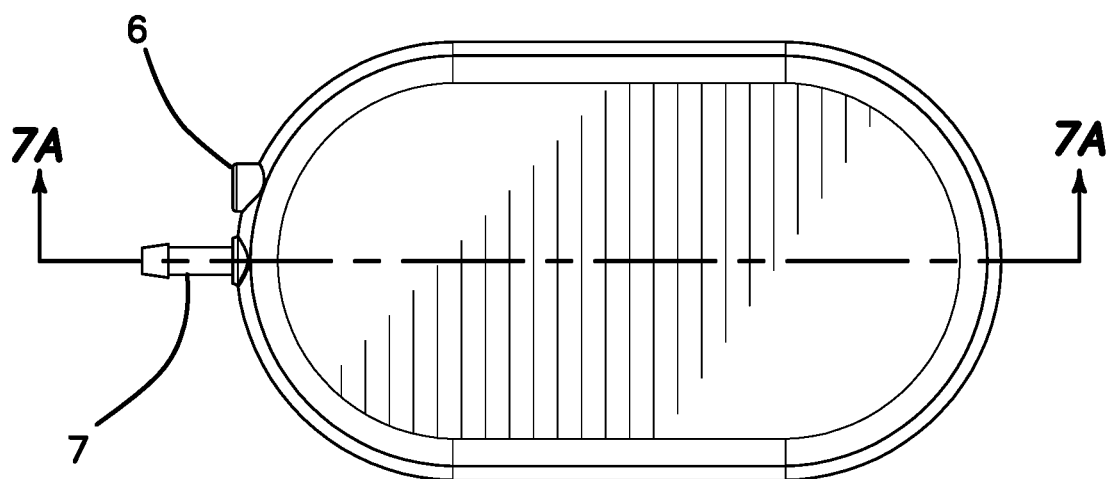
FIG. 7*b* is a top plan view of the SOS of FIG. 1 with the top of the casing in place illustrating section lines 7A-7A.
Figure 7A:
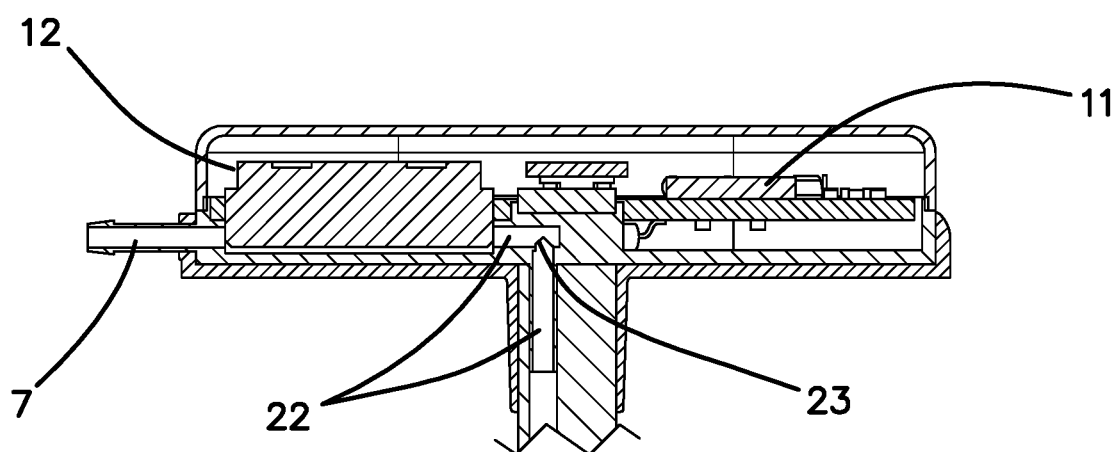
FIG. 7*a* is a side cross sectional view of the assembled SOS of FIGS. 1-5 as seen through section lines 7A-7A if FIG. 7*b*, which are perpendicular to section lines 6B-6B of FIG. 6*b*.
Figure 7A:
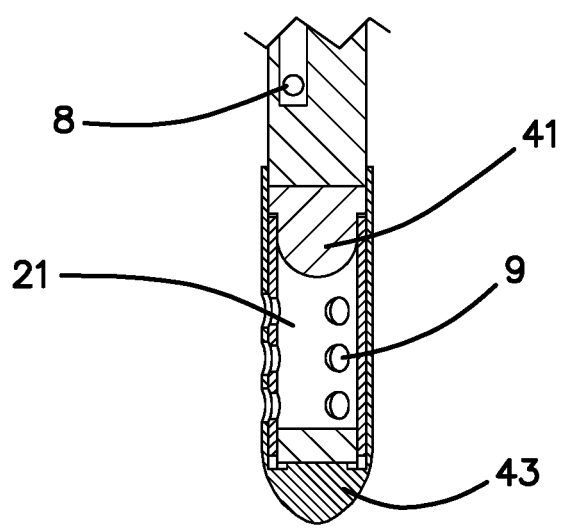

FIG. 7a is a perpendicular side cross sectional view as seen through section lines 7A-7A of FIG. 7b to illustrate a more detailed cross section of the SOS and ventricular catheter 10 highlighting the drug-delivery pathway through the SOS and the ventricular catheter 10 and the pressure sensor 12 in fluidic communication with the ventricular catheter 10. The drug delivered from the ISP 1 through the catheter 2 enters the SOS 3 through the fluid access port 7 via catheter tube 4 and through internal tubing 22, through the drug-delivery connector 23 down the ventricular catheter 10 to the drug delivery port 8. The drug-delivery channel is separated from the sensing chamber 21 to enable drug mixing in the ventricle before it diffuses into the sensing chamber 21 for drug optical sensing (light absorption by drug in the CSF) and the concentration calculation by the electronics 11 (in SOS and ISP).

Figure 8:
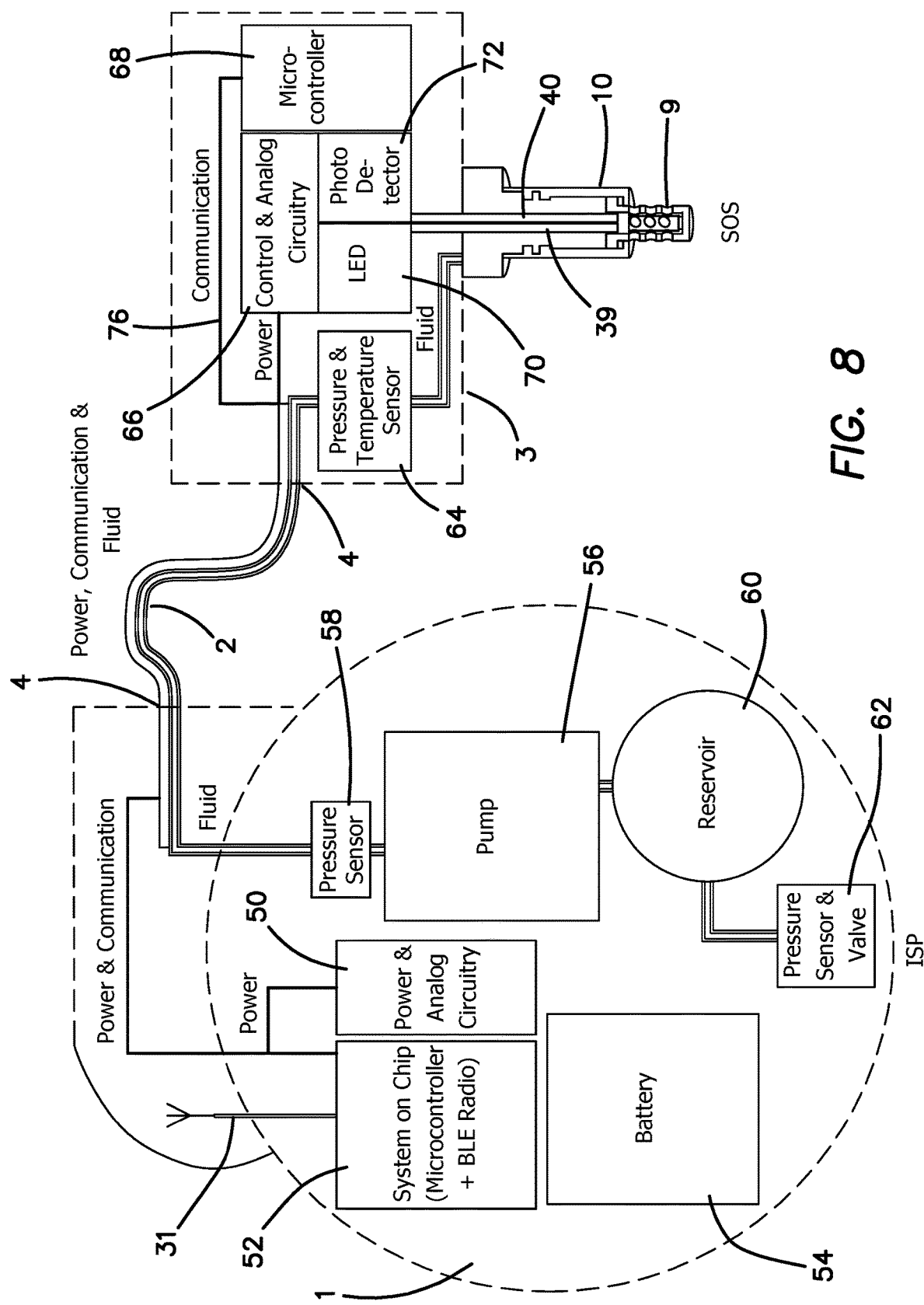
FIG. 8 is a diagram of the main functional elements in the SOS and ISP of FIGS. 1-7.

FIG. 8 is a block diagram of the power, communication and fluid systems for the ISP 1, catheter system and the SOS in the first embodiment. The ISP 1 and SOS 3 illustrated here have distinct functions. The SOS 3 is designed to provide the essential functions for optical sensing and capturing the sensed information. It also houses the drug-delivery channel 22. The ISP 1 is the source of the drug, the wireless communication system, the drug pump, the power, the main computing and analysis electronics and the software. The diagram labels the main components of the ISP 1, the catheter 2, ventricular catheter 10 and the SOS 3. The wired connector in catheter 2 is connected to the electrical connector tips 4 in FIG. 1 on each end the fluid path in catheter 2 illustrated with a white line. The clear line is the drug delivery lumen 4 which is connected to the ISP and through connector 7 to the SOS 3. The dotted lines around the ISP 1 and SOS 3 illustrate the perimeter of each device. ISP 1 includes a battery 54 coupled to the electrical components within ISP 1 and to the SOS 3 via the catheter 2. Power and analog circuitry 50 is coupled to battery 54 to supply the various systems of ISP 1 and SOS 3 with appropriately conditioned power and control signals consistent with conventional design principles. Microcontroller 68 turns on and off the SOS electronics to make measurements, interprets the measurements, converts them into physical units and communicates this information to the ISP 1. All the drug-delivery controls, data logs, alarms and utilization of data is done by the ISP electronics. A microcontroller and Bluetooth low energy (BLE) radio 52 coupled to antenna 31 provides bidirectional control, data and communication signals to and from ISP 1 and SOS 3 and other outputs from the SOS 3 and the power and analog circuitry. The Bluetooth communication 52 will also be in contact with the physician programmer and the mobile system monitor (not illustrated) to enable external monitoring of the pump and SOS function and health. Drugs are stored within reservoir 60 which is coupled to and monitored by pressure sensor and valve 62. The pressure sensor 62 is located at the refill inlet and can detect if the reservoir 60 is over pressured on filling the reservoir 60. The pressure sensor 62 is also used to monitor volume in the reservoir 60 and calculate the amount of drug being delivered and if the delivery is accurate during the refill procedures. Pump 56 is communicated to reservoir 60 and has an output pressure sensor 58 for monitoring the pressure supplied to catheter 2. Outlet pressure sensor 58 will be used to determine if there is a clog in the catheter and correct delivery volume or pressure changes. Drugs are delivered from catheter 2 to SOS pressure and temperature sensor 64, through which the drugs are delivered to catheter 10. Sensor 64 is used in conjunction with pressure sensor 58 to determine if there is an occlusion in the pump catheter or the ventricular catheter 10. Both pressure sensors 58 and 64 together will be used to determine if there is a leak in the pump catheter. Pressure sensor 64 will also be used to measure intercranial pressure (ICP) and trip an alarm to tell the physician if it exceeds a pressure level set by the physician. Brain over-pressure can be a dangerous situation and lead to hydrocephalus. LED bundle 70 and photodetector 72 are coupled to sending optical fiber 39 and receiving optical fiber 40 respectively. LED bundle 70 is powered and controlled by control and analog circuit 66. Photodetector 72 provides an output signal to control and analog circuit 66, which digitizes it and provides it to microcontroller 68. Communication and data signals are bidirectionally supplied to communication line 76 and provided from and to microcontroller and the Bluetooth communication chip and BLE radio 52 via the catheter wires in catheter lumen 5.

Figure 9:
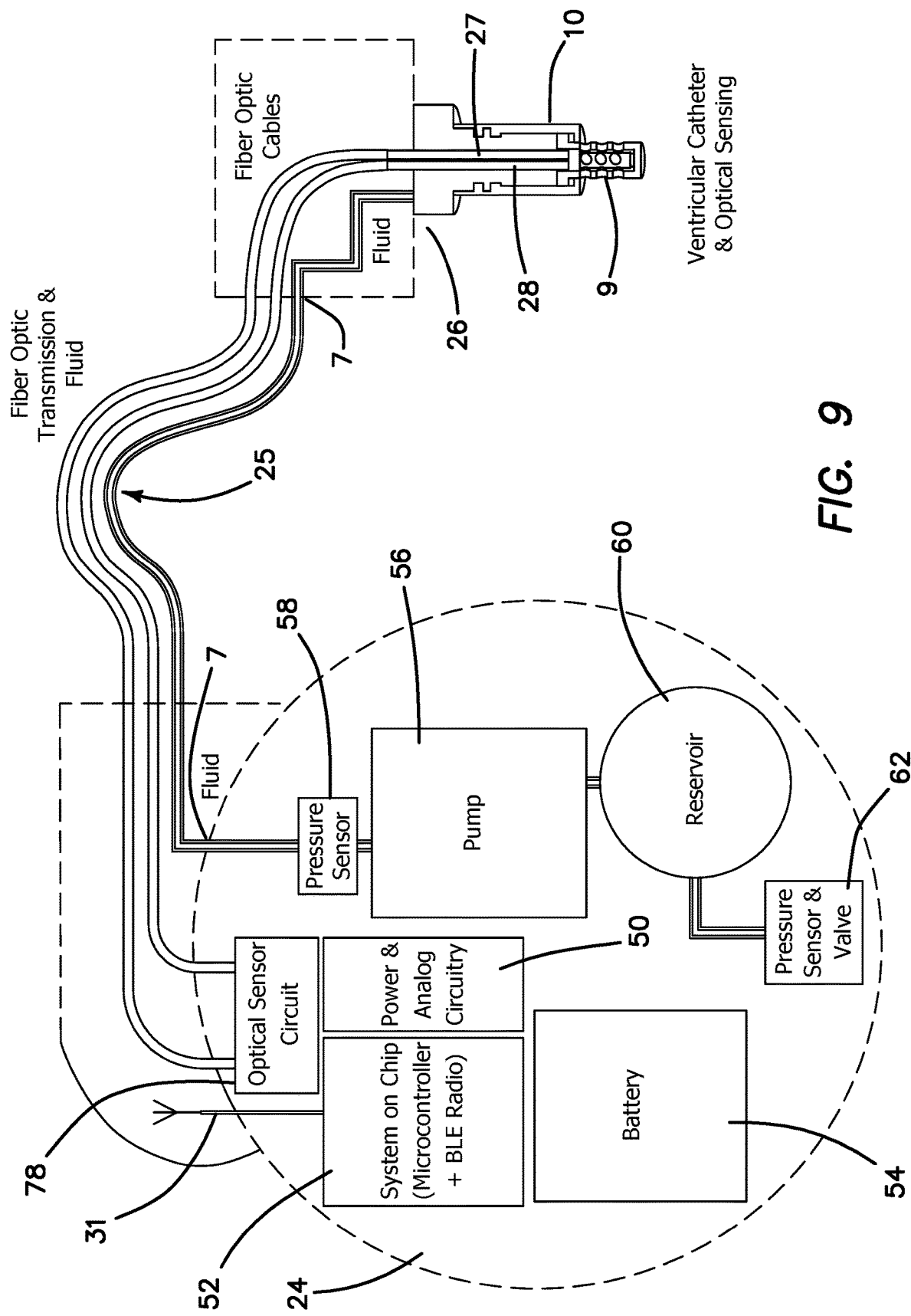
FIG. 9 is a diagram of the main functional elements in the second embodiment of the SOS and MBP.

FIG. 9 is a block diagram of the fiber optic pathways, communication and fluid systems for the MBP 24, tri-lumen catheter system 25 and the skull-mounted ventricular catheter fixture 26 in the second embodiment above. The diagram labels the main components of the MBP 24, the catheter 25 and the ventricular catheter fixture 26. The MBP 24 and ventricular catheter fixture 26 illustrated here have distinct functions. The ventricular catheter fixture 26 is a minimal housing to provide the optical fibers 27 and 28 a conduit from the optical sensor 78 in the MBP 24 through catheter 2 to the sensing chamber 21 and to house the drug delivery catheter 22 to port 8 in the ventricle. The MBP 24 is the source of the drug, the wireless communication system 52, the drug pump 56, the battery power source 52, the optical sensor 18 and LED bundle 17 the main computing and analysis electronics 50 and the software. The advantage of the second embodiment is that the size of the ventricular catheter fixture 26 is significantly reduced. The MBP 24 is necessarily more complex and larger but there will be sufficient room for this change in size at the implantation site. For clarity, the fluid path 4 is connected to the MBP 24 and fixture 26 via the fluid connector 7 in the white line. The fiber optic cables (bolded, dark black lines) for fiber optic sending lead 28 and the fiber optic cable for receiving lead 27 is connected to the ports (unlabeled) on the MBP 24 and fixture 26 respectively. In the second embodiment, the fixture 26 does not collect the data from the optical sensor but rather sends it back directly to the MBP 24 which contains the optical sensor circuitry 78 and the necessary electronics to calculate the drug concentration and process, store and communicate the data. In addition, the pressure sensor system 62, 58 is housed within the MBP 24 and not in the fixture 26 where the fluid path is short. This enables the ventricular fixture 26 to be quite simple and physically small as it will not contain any electronics, the LEDs, or photo diode. In the second embodiment, the fixture 26 is simply a conduit for the drug-delivery catheter 25 and the optical fibers 27, 28 and a fixture to hold them in the proper place with respect to ventricular catheter 10. The main sensing and data management and calculation duties are entirely conducted within the MBP 24.

Figure 10:
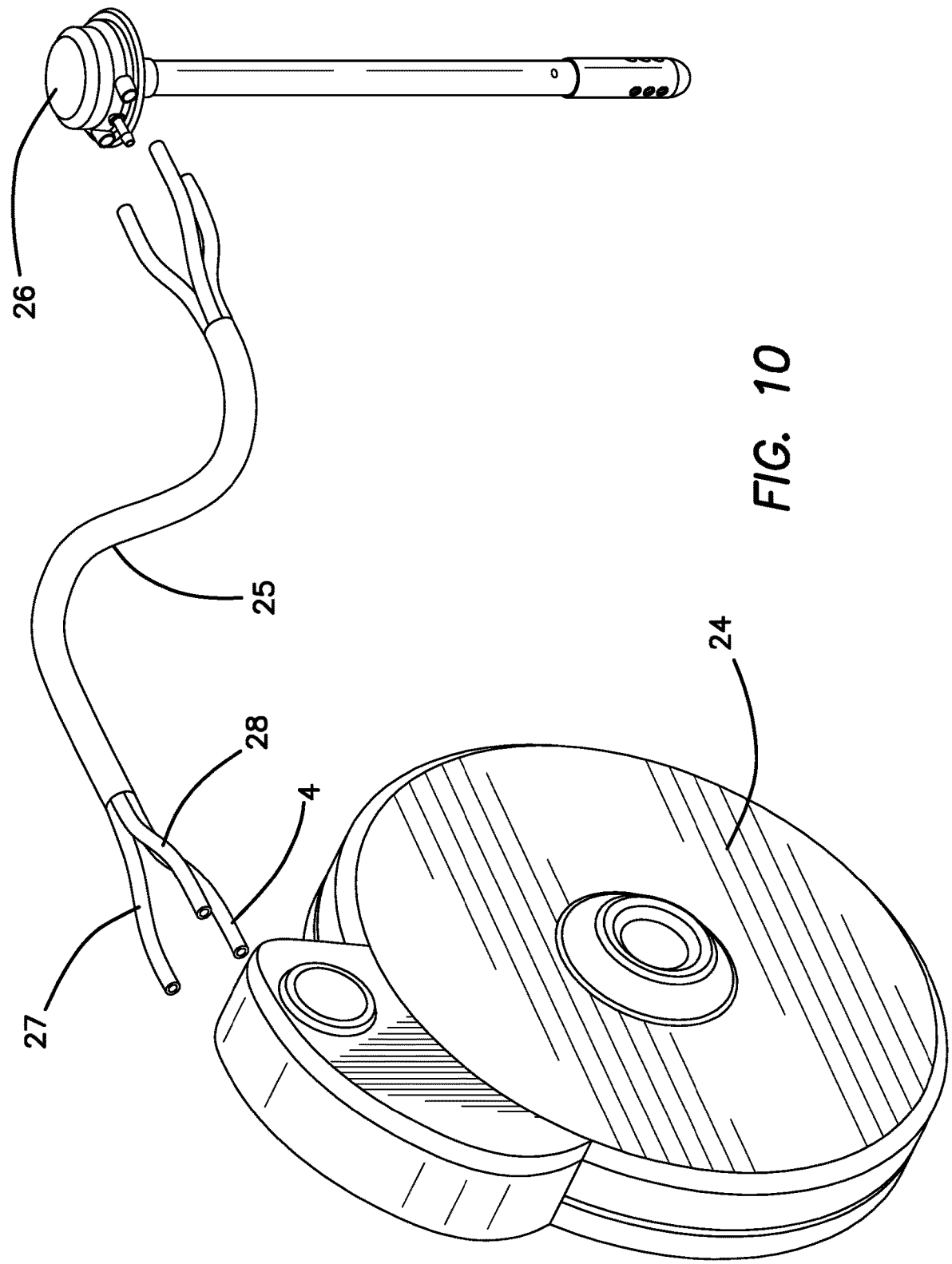
FIG. 10 is an exploded perspective view of the SOS and MBP of the second embodiment.

FIG. 10 is a perspective view of MBP 24, catheter assembly 25 and the skull-mounted ventricular catheter fixture 26. The catheter assembly 25 is a tri-lumen tube containing the drug delivery lumen 4, and the sending fiber optic 28 and the receiving fiber optic 27.

Figure 11:
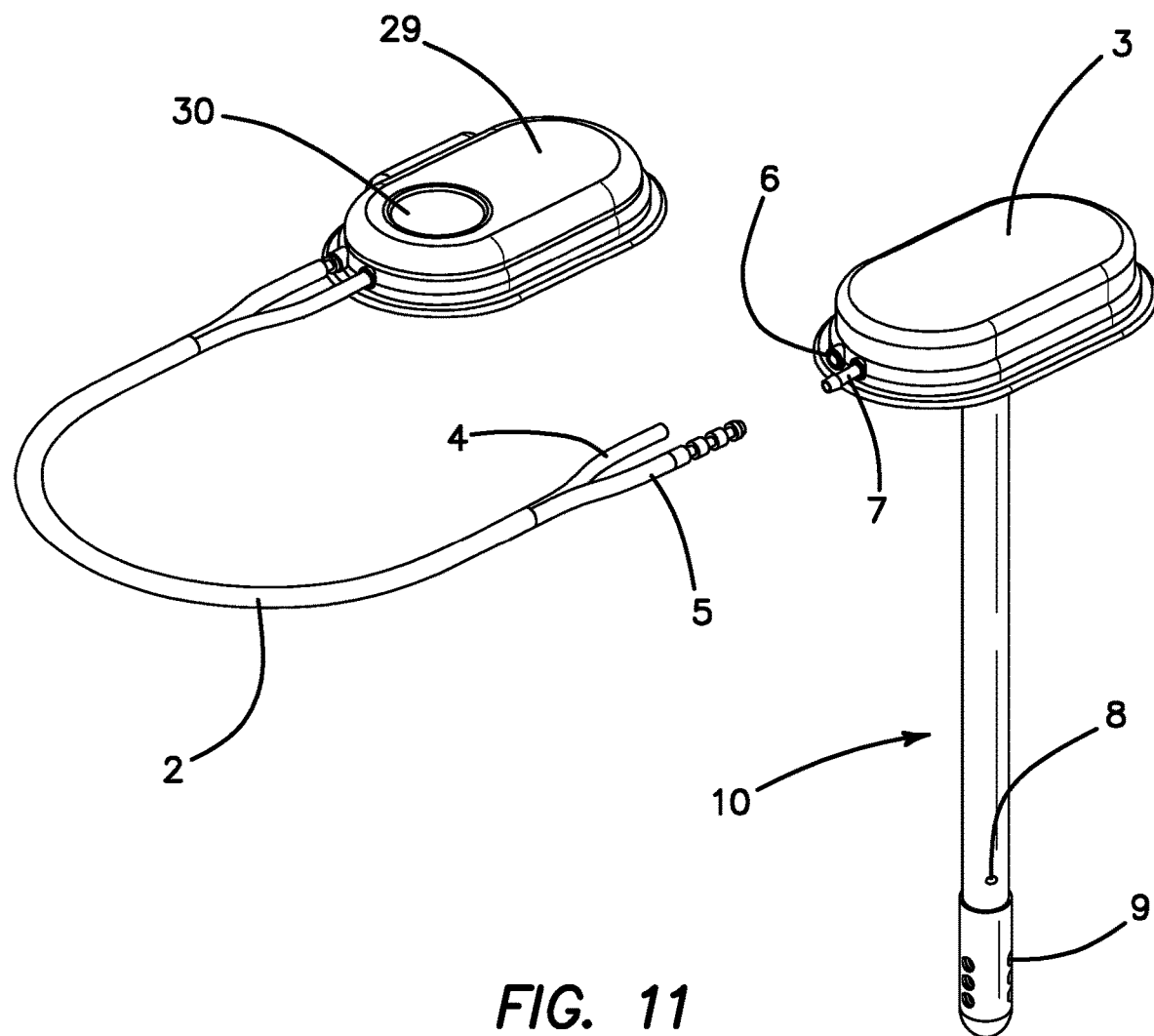
FIG. 11 is an exploded perspective view of the SOS and PCU of the third embodiment.

FIG. 11 is a perspective view for third embodiment above which is a "stand-alone" system that consist of SOS 3 and the dual lumen catheter 2 connected to a power and communication unit (PCU) 29 which enables the SOS 3 to operate without connection to the ISP 1. The PCU will enable the SOS sensor to be independent by providing power, electronics and communication capabilities. Optionally the SOS 3 could also be used as an independent sensor and work through external communication with other properly designed drug-delivery systems. In the third embodiment, the PCU 29 provides the power, electronic data collection, management, calculations and wireless communication that will enable external communications with the clinician programmer, patient mobile system monitor (not shown), cloud-based EMR storage database and optionally the ISP 1 to close a data feedback loop based on the drug and pressure information received from the SOS 3. FIG. 11 shows the PCU 29 contains a self-healing septum covering the ventricular access port 30 that communicates through drug delivery lumen 4 of catheter 2 to the SOS 3 and delivers drug through the drug delivery port 8 using an external syringe or external pump connected through the skin and into the ventricular access port 30. It should be pointed out another intended use of the ventricular access port 30 is to withdraw CSF fluid should there be brain high pressure (potential hydrocephalus) or if the doctor wishes to analyze CSF directly from the patient. A wired connection from the SOS 3 goes through connector 6 to wire 5 to the PCU 29 and provides the power needed to operate the SOS electronics, LEDs, photo diode and other necessary functions in the SOS 3 as well as the PCU 29 power requirements. The SOS 3 and catheter 2 in first and third embodiments are the same. The differences between these two embodiments is that the power and communications are done in the ISP 1 or PCU 29 respectively.

Figure 12:
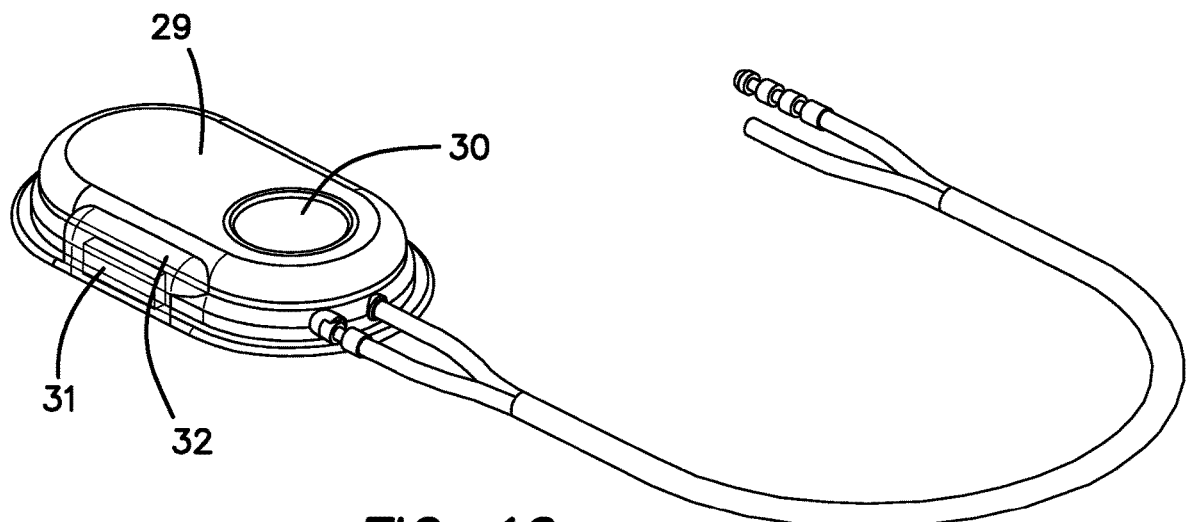
FIG. 12 is an enlarged perspective view of the PCU of FIG. 11 shown connected to its multilumen tubing and electrical connector.
Figure 13:
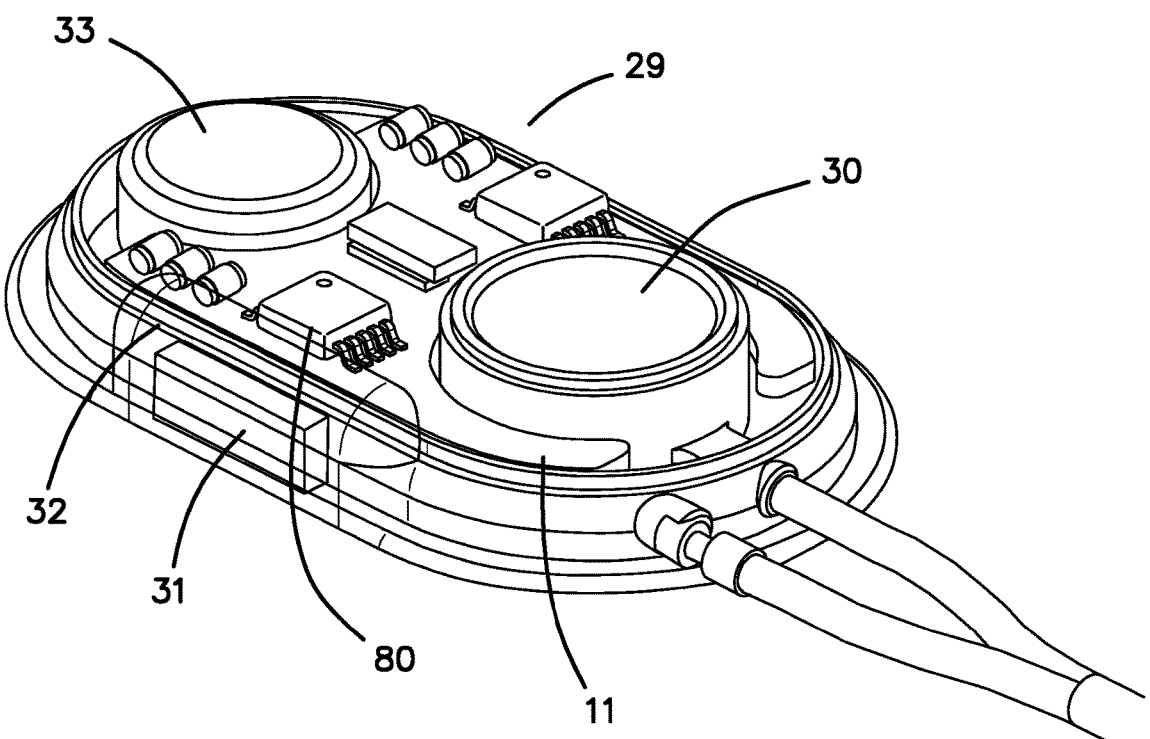
FIG. 13 is an enlarged perspective view of the PCU of FIG. 12 shown with the top cover removed to illustrate the battery, electronics and ventricular access port included therein.

FIG. 12 is a perspective drawing showing the Bluetooth antenna 31 and the antenna holder 32. FIG. 13 is a perspective drawing of the PCU 29 with the top cover removed to provide more detail about the internal components. The PCU 29 includes a battery 33, ventricular access port 30, the Bluetooth communication chip 80 on the electronics board 11 connected to the Bluetooth antenna holder 32 and the Bluetooth antenna 31.

Figure 14:
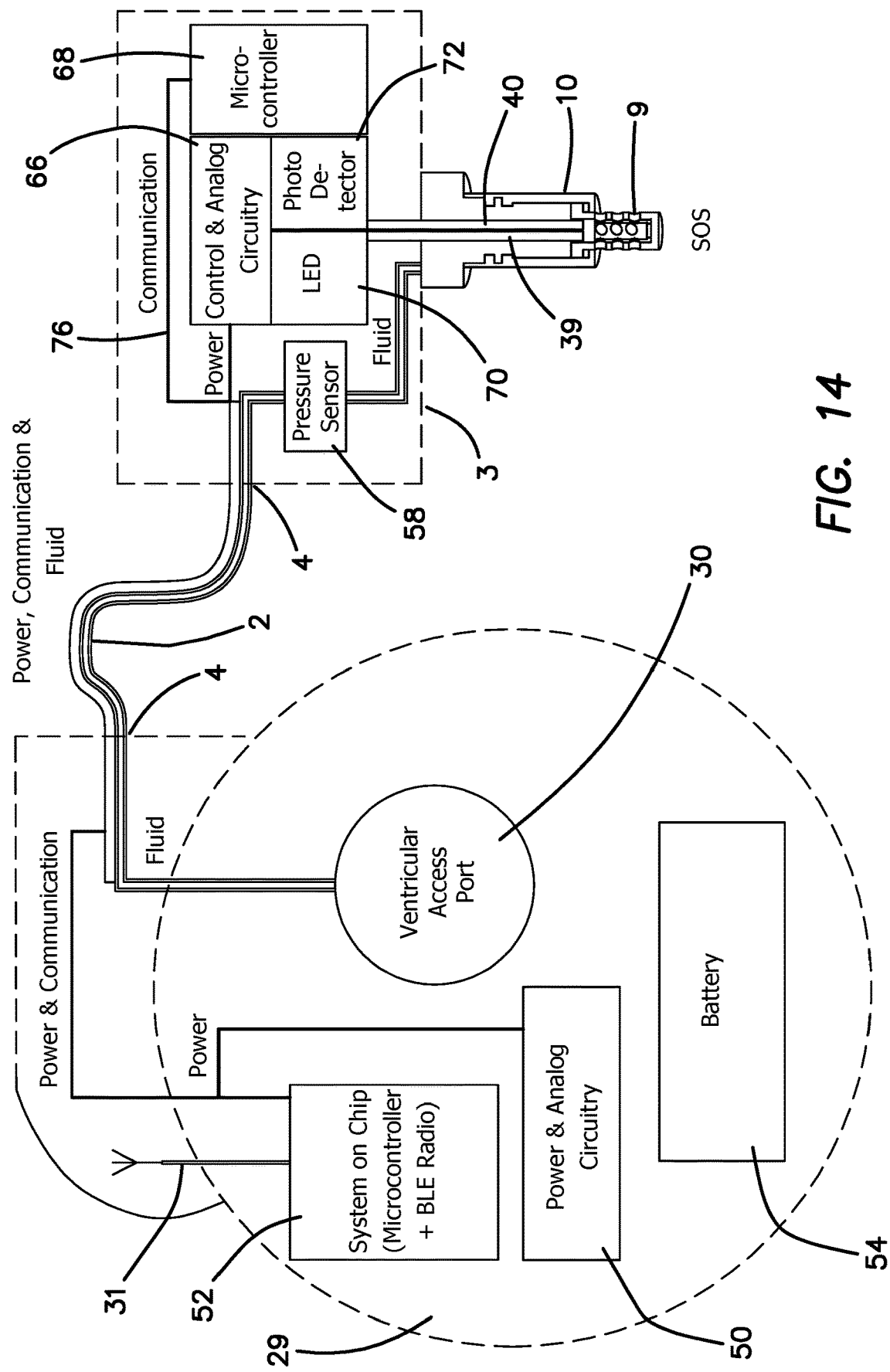
FIG. 14 is a diagram of the main functional elements in the third embodiment of the SOS and PCU of FIGS. 11-13.

FIG. 14 is a block diagram of the power, communication and fluid systems for the PCU 29, catheter system 2 and the SOS 3 in third embodiment. The diagram labels the main components of the PCU 29, the catheter 2 and the SOS 3. For clarity, the wired connector is in a black bold line in catheter 2 and is connected to the electrical connector tip 4 on each end the fluid path is illustrated with a white line. The dotted lines around the PCU 29 and SOS 3 illustrate the perimeter of each device. As in the prior embodiments, PCU 29 includes a battery 54, power and analog circuitry 50, microcontroller and BLE radios 52, and antenna 31. VAP 30 is included in PCU 29 and the components of PCU 29 are communicated to SOS 3 through catheter 2. SOS 3 includes pressure sensor 58 communicated to ventricular catheter 10. LED 70, photodiode 72, control and analog circuitry 66 and microcontroller 68 as in the prior embodiments are included in SOS 3. The SOS 3 in first and third embodiments are the same.

Figure 15:
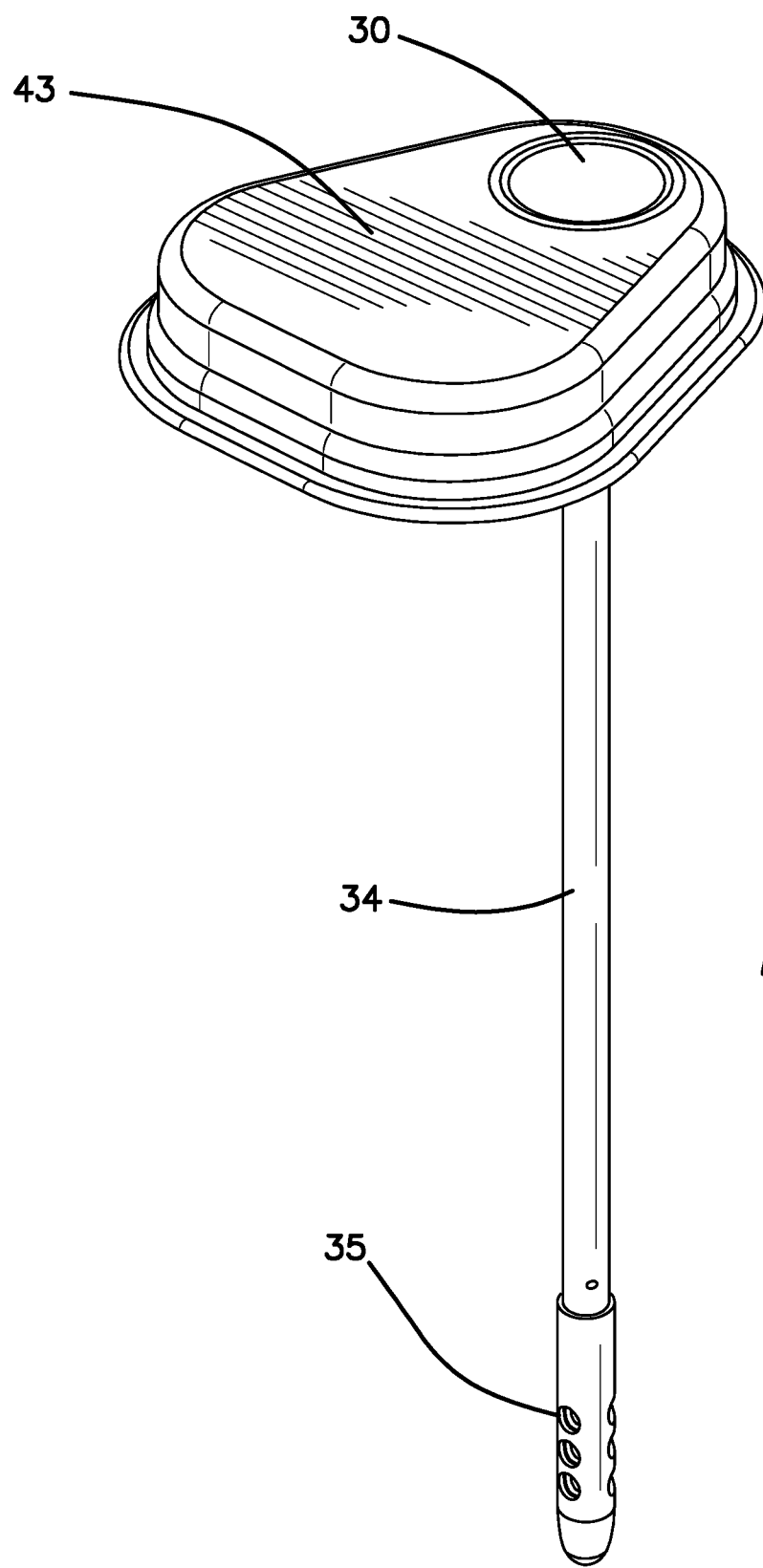
FIG. 15 is a perspective view of the stand-alone skull-mounted pressure sensor (SPS) with a ventricular access port of the forth embodiment.

Under certain circumstances during chemotherapy brain pressure builds up and if left untreated can become a serious medical concern and if not returned to normal will result in hydrocephalus. The fourth embodiment addresses this using a smart device that measures brain pressure and temperature and communicates it to a clinician programmer and a mobile system monitor. Medical personnel so informed can then take appropriate action. The skull-mounted pressure sensor (SPS) 43 also contains a ventricular access port 30 to enable the removal of CSF fluid, measure drug in CSF or deliver drugs into the ventricle. FIG. 15 is a perspective drawing of the stand-alone skull-mounted pressure sensor (SPS) 43 of the fourth embodiment illustrating the VAP 30, the ventricular catheter 34 that is in fluid communication with the CSF access ports 35, the pressure/temperature sensor 12 and the VAP 30 shown in FIG. 16. The fourth embodiment does not contain optical sensors as its primary function is to determine CSF pressure and temperature and not to calculate drug concentration in CSF. It does contain the VAP 30 to provide the medical personnel convenient options should brain pressure be found to be elevated.

Figure 16:
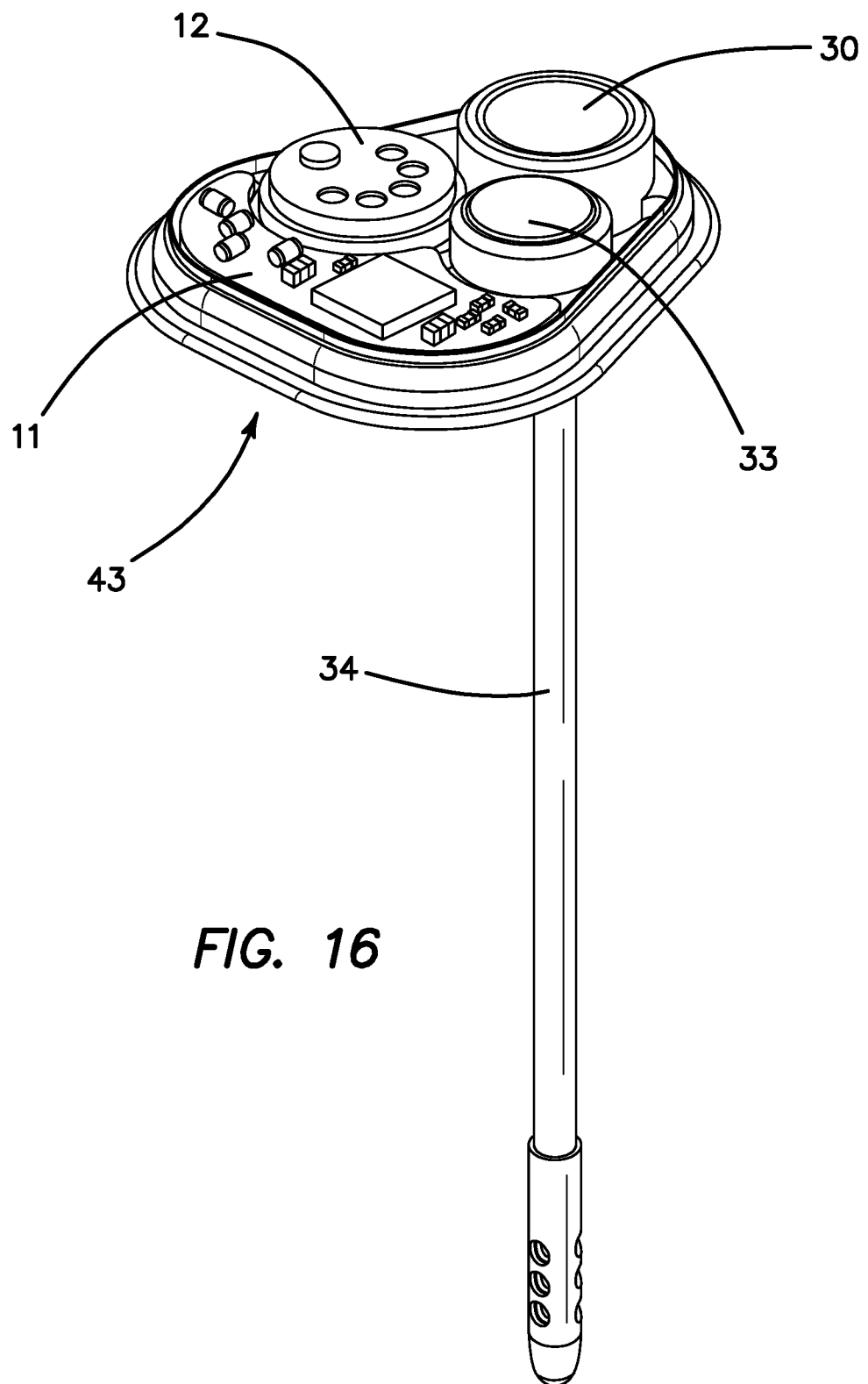
FIG. 16 is a perspective view of the stand-alone skull-mounted pressure sensor (SPS) of FIG. 15 with the top cover removed to show the pressure sensor, ventricular access port (VAP), battery and electronics therein.

FIG. 16 is a cut-away drawing of the SPS 43 with the top removed to show the main components on the skull-mounted portion. The SPS 43 has a battery 33 to power the electronics board 11, a pressure sensor 12 in fluid communication with the VAP 30 and the ventricular catheter 34. FIG. 17a is a side cross sectional view of the SPS 43 as seen through section lines 17C-17C of FIG. 17b. FIG. 17a illustrates in more detail the fluid pathway from the pressure sensor 12 through the VAP chamber 36 to the ventricular catheter 34 via a fluid path 37 in VAP catheter 34, through VAP septum 39, VAP chamber 36, the CSF chamber 38, the CSF access ports 35. The CSF access port 35 enables fluid communication between the CSF chamber 38 and the CSF in the ventricle.

Figure 18:
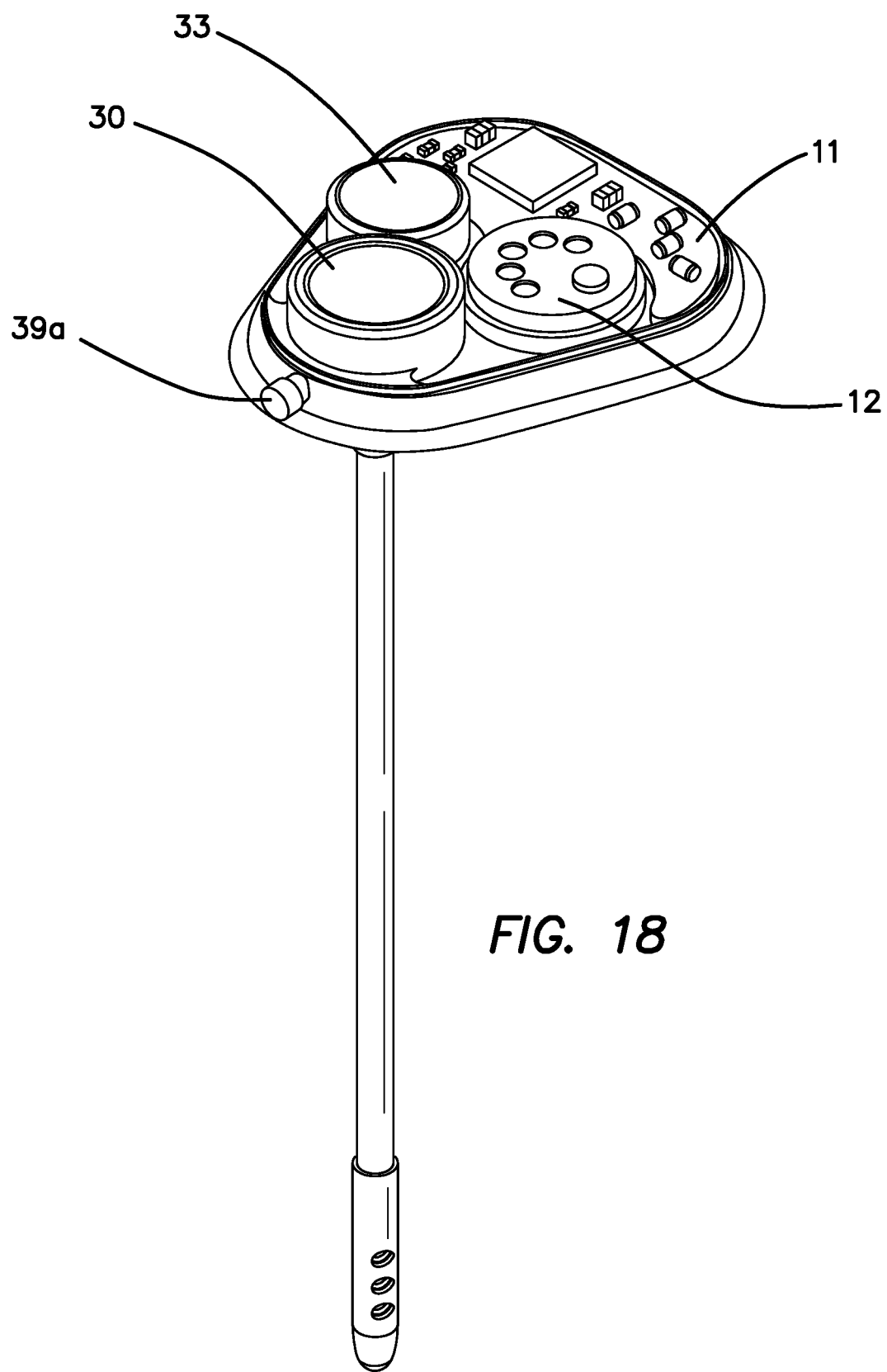
FIG. 18 is a perspective view of a sub-embodiment of fourth embodiment with the top cover removed that enables the optional drainage of CSF through a magnetically adjustable valve (a leak) to relieve high CSF pressure and reduce the potential of developing hydrocephalus.
Figure 19:
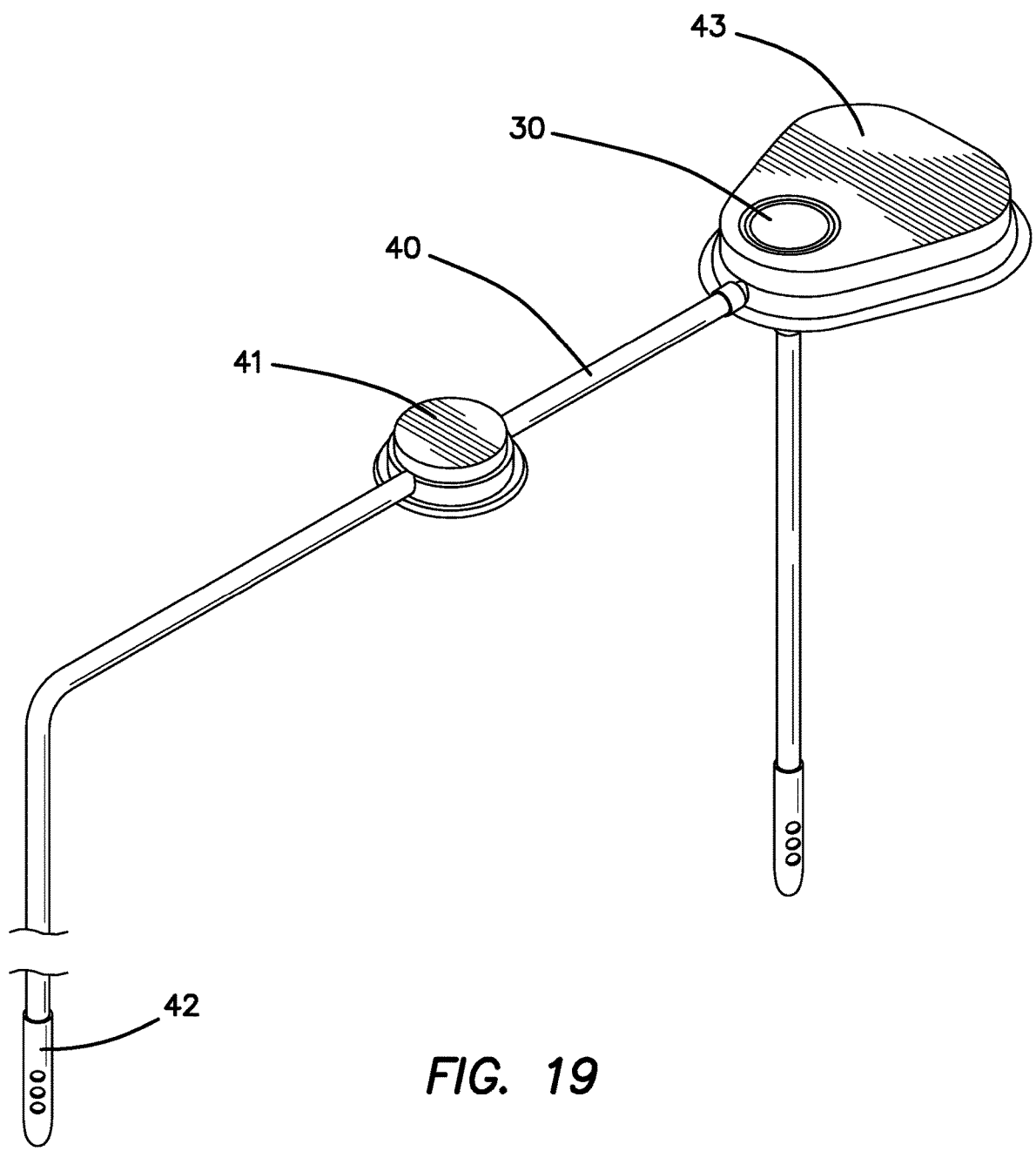
FIG. 19 is a perspective view of the sub-embodiment of FIG. 18 connected to a magnetic valve and peritoneal catheter tip.

The SPS 43 may optionally have a connector 39a from the VAP 30 to the exterior of the SPS 43 which may be capped to prevent leakage from the VAP 30 as shown in FIG. 18. The connector 39a is in fluid communication with the VAP 30, the pressure sensor 12 and the brain catheter 34. The cap on the connector prevents leakage from the CSF until it is removed. The cap on the connector 39a can be optionally removed and connected to a variety of catheter options depending on the medical indication. Optionally and most preferred when needed to reduce brain pressure, connector 39a may be uncapped and connected to a catheter assembly 40 that has sufficient length to drain into the peritoneal cavity as shown in FIG. 19. The catheter assembly 40 is optionally fitted with a valve 41 that can be magnetically adjusted to enable a prescribed CSF leak rate to enable brain pressure reduction. Other kinds of valves can also be employed such as passive flap valves designed to leak at certain pressures and mechanical valves that can be adjusted through the skin. The tip of the catheter 42 is placed in the peritoneal cavity to enable the leaked CSF to drain into the peritoneal cavity and relieve excess brain pressure. In this configuration, the PSP 43 acts like a hydrocephalus shunt.

Measurement of drug concentration in a sample is based on the relationship described by the Beer-Lambert equation, which states that the attenuation of a light source when passed through a sample solution is related to the concentration of material present in the solution. In the SOS 3 of the first embodiment FIGS. 1-8, multiple LED sources are used that emit at specific frequencies in the UV/VIS range. These frequencies are chosen to maximize sensitivity, as drugs strongly absorb in the selected LED emission range. In total and for this example, the system contains four LED's of drug specific light frequencies. The system could have fewer or more LEDs depending on the complexity of the desired analysis. This gives the system flexibility to be modified according to the needs to measure a specific drug or a group of drugs or natural components found in the CSF. This optical analysis system could be used in other locations in the body where there is an extracellular fluid for which the concentration of a fluid component (for example a drug, protein, hormone, etc.) is to be measured. This UV/VIS light is transmitted as shown in FIG. 6 via a fiber-optic 39 to the CSF chamber 21 at the end of the brain catheter 10 segment. This chamber 21 includes a perforated wall 9 to allow CSF fluid to freely move in and out of the chamber 21, while preventing any brain tissues that could obstruct the light path from entering.

From the end of the transmitting fiber-optic 39, the UV/VIS light will pass through a lens 41, pass through the CSF in chamber 21, be reflected back from mirror 42 through the sensing chamber 21, through the lens 41 and returned by fiber optic cable 40 to the receiving photo diode (sensor) 15. The mirror 42 is a double 90° reflection of a conical mirror. The fiber optic cable 40 will carry the returned UV/VIS light to a UV/VIS light sensor 15. Here, the light intensity will be converted to an electrical signal proportional with the UV/VIS light intensity. The analog signal will then be amplified, filtered and converted to a digital format by the onboard electronics, generally denoted by reference numeral 11 best shown in FIG. 3.

In the first embodiment, the SOS only communicates through wires to the ISP 1 via catheter 2 and the onboard electronics is to manage LEDs, the data collection and storage from the sensor and a variety of housekeeping duties. FIG. 2 illustrates the SOS's connector fittings for the catheter wires 6 and the drug delivery connector 7.

The embedded micro-controller and Bluetooth controller 52 in the third embodiment provide the bidirectional data communication, data measurement schedule and data storage. The internal button lithium battery 54 provides the necessary operating power. To conserve energy, the electronics hardware 50, 52 will spend the majority of the time in "sleep mode".

Since the absorption spectra of most drugs features at least one prominent peak, the UV/VIS LEDs frequencies can be selected to cover optionally one or more leading edges of selected peaks one or more major peak maxima, optionally one or more trailing peak edges and a neutral reference—where absorption does not change with drug concentration—over the drug specific frequencies range.

The optical sensor has one or more LEDs depending on the requirements of a predetermined analysis complexity. For more flexibility and for general applications the number of LEDs can be increased to cover a wider range of wavelengths and sensitivities. For the current devices illustrated but not limited to these examples the optimum number of LEDs was settled on four to three for absorption measurement and one as a calibration and reference LED. The optical sensor can be customized to measure any optical absorption profile and for any wavelength for which LEDs are available. This makes the optical sensor a remarkably flexible, implantable drug sensor with a very wide range of potential measurement applications. When a measurement is made, each LED is turned on individually (in sequence) one at a time and a measurement is made. The peak LED measurement will be used to calculate the absorption and consequently the drug concentration. The leading and trailing LEDs will provide the drug specificity measurement. The reference LED will measure the baseline value, which is made possible by selecting a frequency that is not absorbed by the drug and the selected fluid. Inside the LED package 70 there is a photo-diode 72. This photo-sensor measures the package window reflected light which is used as the feedback signal to an optional constant light closed loop circuit included in electronics. This optional constant light regulation minimizes the LED chip amplitude drift and allows for a relative fast measurement cycle. The LED low power and fast measurements eliminates any UV/VIS effect on the CSF or other fluid and increases the battery operating time.

The pressure sensor has three main uses. The pressure/temperature sensor in the first and second embodiments will optionally monitor the system for leaks in the drug delivery catheter, clogged catheter and CSF pressure and temperature. CSF pressure is sometimes elevated during cancer chemotherapy to the brain and it is an important added feature to inform medical personnel when it is elevated. In the third embodiment where there is a PCU it will not be necessary to monitor for a leak and in this embodiment the pressure/temperature sensor will be absent. In the fourth embodiment, the PSP, the pressure/temperature sensor will monitor CSF pressure only as there is no pumping drug delivery pathway only a ventricular access port for optional drug delivery or CSF sampling.

The SOS 3 can be used in the following cancer applications:
  Intrathecal therapy where it's important to monitor the local drug concentration at the site where the drug is delivered (applies to all forms of cancer that have spread to the brain) where CSF flow has been verified.
  For use in the cavum septum pellucidum (CSP) because measurements of the concentration of chemotherapeutic agent by the SOS 3 can verify CSF patency (normal CSF flow) based on the fact that drug concentrations would get to be too high.

Risks associated with current SOS reservoir design include:
  The most common risks associated with the use of the SOS reservoir primarily deal with complications due to malposition or malfunction of the device. Either condition may result in blockage or leakage of the catheter 10, leading to improper drug delivery.
  Lesions may develop along the catheter 10, infection may develop, and chemotherapy may reach toxic levels.
  In cancer patients scheduled for surgical intervention, who have previously received chemotherapy via an Ommaya or SOS reservoir, there is some evidence of increased perioperative (between admission and discharge from hospital) morbidity due to a diseased condition existing at the time of surgery with Ommaya reservoirs.

There are several additional embodiments of this invention and the extensions of these modified embodiments. For example, the apparatus could be made without a drug delivery cannula from the ISP 1 or catheter 2 built into the SOS as described in the third embodiment. Then the optical sensor would still operate but only measure internal CSF fluids or drugs in CSF fluids administered separately through an external cannula or via a systemic route that gets to the brain via the circulation system. This embodiment would still have a cannula from the PCU's VAP 30 for adding drugs via an external pump or syringe from the VAP 30 or for withdrawing fluids from the CSF. The opportunities for utility go well beyond cancer as this could be delivering drugs or monitoring drugs for Parkinson's Disease, epilepsy, bipolar disease, Alzheimer's Disease, schizophrenia and depression where patient compliance is an issue and other CNS and neurodegenerative diseases.

The metronomic biofeedback pump 24 (MBP or ISP) is a fully implantable smart infusion device (ISP 1 or implanted smart pump), designed to locally deliver chemotherapies or medication over time to a target site. Then this would make the pump purely a single pump system.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

In the illustrated embodiments only drug delivery into the brain ventricle is disclosed. With a different catheter designs drugs could be delivered into any tissue in the brain, elsewhere in the body or into a solid tumor where the optical chamber 21 would optionally be omitted. Delivery of drugs into any area of the brain is expressly contemplated as within the scope of the invention, namely for various noncancerous diseases such as Parkinson's Disease, depression, epilepsy, schizophrenia bipolar disease, neurodegenerative diseases by regular or more importantly by convection enhanced delivery (CED). CED is a therapeutic strategy that was developed to facilitate targeted delivery of pharmaceuticals to the brain. The CED procedure involves a minimally invasive surgical exposure of the brain, followed by placement of small diameter catheters directly into the brain tumor. Subsequently, infusion of therapeutics into the tumor occurs over several hours to saturate the target tissue. As this approach effectively bypasses the blood-brain-barrier, it allows for delivery of macromolecular drugs that would not normally enter the brain to effectively reach high concentrations within brain tumor tissue. In order to reach similar concentrations as those achieved with CED, systemically administered conventional chemotherapeutic agents would need to be given at doses that would result in significant toxicity. Thus, an additional benefit of CED is that it simultaneously limits exposure of the remainder of the body to the therapeutic agent and thus minimizes systemic drug-related adverse effects. CED is an important delivery method for brain and tissue delivery. In general for CED only the catheter tip disclosed above would need to be changed.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. An apparatus comprising:
    an implantable skull-mounted drug and pressure sensor (SOS);
    a metronomic biofeedback pump (MBP) electrically coupled to the SOS;
    a drug delivery and communications catheter having a sending and receiving optical fiber communicating the SOS with the MBP,
    where the SOS comprises:
        an optical ventricular catheter comprising a drug delivery port and a CSF optical sensing chamber communicated with the sending and receiving optical fibers included in the drug delivery and communications catheter;
        an LED bundle coupled to the optical ventricular catheter, the LED bundle comprising a plurality of LEDs which are each configured to measure at least one optical absorption profile of cerebrospinal fluid (CSF); and
        a photodetector coupled to the optical ventricular catheter,
        where the CSF optical sensing chamber is configured to receive light from the LED bundle and reflect it back to the photodetector, and
    where the MBP includes a drug reservoir, a pump communicated to the drug reservoir, a first pressure sensor coupled to the pump, an optical source and sensor circuit coupled to the sending and receiving optical fibers, and a first microcontroller subsystem for controlling the pump and bidirectionally communicating with the first pressure sensor and pump and the optical source and sensor circuit,
    where the SOS further comprises a second microcontroller subsystem for controlling the LED bundle and photodetector, wherein the second microcontroller subsystem communicates a measurement detected by the photodetector to the first microcontroller subsystem.

2. The apparatus of claim 1 where the first microcontroller subsystem for controlling the pump and bidirectionally communicating with the first pressure sensor and pump comprises:
    a microcontroller;
    a Bluetooth radio coupled to the microcontroller;
    an antenna coupled to the Bluetooth radio;
    a power and analog circuit coupled to the optical source and sensor circuit, microcontroller and Bluetooth radio; and
    a power source coupled to the pump, to the microcontroller, to the Bluetooth radio, to the optical source and sensor circuit and to the first pressure sensor.

3. The apparatus of claim 1 further comprising a second pressure sensor coupled to the reservoir and communicated to the first microcontroller subsystem, the second pressure sensor including a selectively operated valve.

* * * * *